United States Patent
Jensen et al.

(10) Patent No.: US 7,503,902 B2
(45) Date of Patent: Mar. 17, 2009

(54) BLOOD FLOW REVERSAL VALVES AND RELATED SYSTEMS AND METHODS

(75) Inventors: Mel Jensen, Westhaven, UT (US); Lynn E. Jensen, Syracuse, UT (US); Thomas I. Folden, Alamo, CA (US); John Oliver, Ogden, UT (US); Olli Tuominen, Kowloon Tong (HK)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 11/246,724

(22) Filed: Oct. 6, 2005

(65) Prior Publication Data
US 2006/0079827 A1    Apr. 13, 2006

Related U.S. Application Data

(60) Provisional application No. 60/616,794, filed on Oct. 7, 2004.

(51) Int. Cl.
*A61M 37/00* (2006.01)
*A61M 1/00* (2006.01)
*F16K 51/00* (2006.01)

(52) U.S. Cl. ............... 604/6.1; 604/6.01; 604/6.16; 604/32; 422/44; 251/149.2

(58) Field of Classification Search ........ 604/4.01–6.16, 604/27–30, 32, 34, 40, 43, 153, 905, 248, 604/246, 93.01; 422/44–48; 606/192–194; 137/625.43, 625.44, 625.14, 625, 625.42, 137/597, 625.12, 625.13, 625.15, 625.46, 137/802, 247, 247.11, 247.13, 251.1, 252–254, 137/455, 625.28, 625.32; 210/425, 424–5, 210/93, 118, 137, 141; 251/12, 142, 149, 251/149.2, 149.5, 149.6, 205, 208, 304
See application file for complete search history.

(56) References Cited

U.S. PATENT DOCUMENTS

| | | | |
|---|---|---|---|
| 3,157,201 A | * | 11/1964 | Littmann ............... 137/625.47 |
| 3,626,938 A | | 12/1971 | Versaci |
| 4,397,335 A | | 8/1983 | Doblar et al. |
| 4,695,385 A | | 9/1987 | Boag |

(Continued)

FOREIGN PATENT DOCUMENTS

| | | |
|---|---|---|
| DE | 19528907 | 11/1996 |
| EP | 1106191 A1 | 6/2001 |
| WO | WO99/64088 | 12/1999 |
| WO | WO2005/061043 | 7/2005 |

OTHER PUBLICATIONS

Mercadal et al., Determination of Access Blood Flow From Ionic Dialysance: Theory and Validation, Kidney Int'l, vol. 56 (1999), pp. 1560-1565.

Nikolai M. Krivitski, Novel Method to Measure Access Flow During Hemodialysis by Ultrasound Velocity Dilution Technique, ASAIO Journal, Jul.-Sep. 1995, vol. 41, No. 3 at M741.

Paul G. Sakiewicz, Emil P. Paganni, and Eugene Wright, Introduction of a Switch that Can Reverse Blood Flow Direction On-Line during Hemodialysis, ASAIO Journal 2000 at 464.

Thomas A. Depner and Nikolai M. Krivitski, Clinical Measurement of Blood Flow in Hemodialysis Access Fistulae and Grafts by Ultrasound Dilution, ASAIO Journal, Jul.-Sep. 1995, vol. 41, No. 3 at M745.

(Continued)

*Primary Examiner*—Leslie R Deak
*Assistant Examiner*—Phil Wiest
(74) *Attorney, Agent, or Firm*—Fish & Richardson P.C.

(57) ABSTRACT

A blood flow reversal valve useful in hemodialysis having rotational detent features enabling audible and tactile feedback to a clinician and alignment features such as visible indicators associated with the blood lines on either side of the valve to confirm normal or reverse flow.

39 Claims, 12 Drawing Sheets

U.S. PATENT DOCUMENTS

| | | | |
|---|---|---|---|
| 4,821,996 | A | 4/1989 | Bellotti et al. |
| 4,885,087 | A | 12/1989 | Kopf |
| 4,898,669 | A * | 2/1990 | Tesio .................... 210/232 |
| 4,904,245 | A | 2/1990 | Chen et al. |
| 5,082,025 | A | 1/1992 | DeVries et al. |
| 5,135,026 | A * | 8/1992 | Manska .................. 137/555 |
| 5,392,772 | A | 2/1995 | Zilbershtein |
| 5,605,630 | A | 2/1997 | Shibata |
| 5,685,989 | A | 11/1997 | Krivitski et al. |
| 5,830,365 | A | 11/1998 | Schneditz |
| 5,894,011 | A * | 4/1999 | Prosl et al. ............... 422/44 |
| 6,177,049 | B1 | 1/2001 | Schnell et al. |
| 6,308,737 | B1 | 10/2001 | Krivitski |
| 6,319,465 | B1 * | 11/2001 | Schnell et al. ............ 422/44 |
| 6,596,234 | B1 | 7/2003 | Schnell et al. |
| 6,695,807 | B2 | 2/2004 | Bell et al. |
| 6,726,647 | B1 | 4/2004 | Sternby et al. |
| 6,726,663 | B1 * | 4/2004 | Dennis ................ 604/164.11 |
| 7,384,543 | B2 | 6/2008 | Jonsson et al. |
| 2001/0031222 | A1 | 10/2001 | Schnell et al. |
| 2003/0018290 | A1 | 1/2003 | Brugger et al. |
| 2003/0138348 | A1 | 7/2003 | Bell et al. |
| 2005/0145549 | A1 | 7/2005 | Jonsson et al. |
| 2005/0178732 | A1 | 8/2005 | Krivitski et al. |

OTHER PUBLICATIONS

Thomas A. Depner, Nikolai M. Krivitski, and David MacGibbon, Hemodialysis Access Recirculation Measured by Ultrasound Dilution, ASAIO Journal, Jul.-Sep. 1995, vol. 41, No. 3 at M749.

Fresenius Combilines with Access Flow Reversing Connector 510(k) Submission; 2002.

"Reverso Flow Reversing Interconnector" Brochure, *Medisystems HemoDYNAMIC Devices*, 2000.

* cited by examiner

BLOOD FLOW REVERSAL VALVES AND RELATED SYSTEMS AND METHODS

CROSS-REFERENCE TO RELATED APPLICATIONS

This application claims the benefit of U.S. Provisional Application No. 60/616,794, filed Oct. 7, 2004 and entitled "Blood Flow Reversal Device for Hemodialysis," which is incorporated by reference herein.

TECHNICAL FIELD

This invention relates to blood flow reversal valves and related systems and methods.

BACKGROUND

Many modern medical procedures use tubing sets of varying complexity to withdraw fluid from a patient, or to administer fluid to a patient, or to do both. One example of such a procedure is hemodialysis. In hemodialysis, the patient's blood is cleansed by drawing it out of the patient through a blood access site, typically via a catheter, and passing it through an artificial kidney (often called a "dialyzer"). The artificial kidney includes a semi-permeable membrane which removes impurities and toxins by a process of diffusion. The purified blood is then returned to the patient. An extracorporeal circuit including a pump and hemodialysis tubing set is typically used to transport the blood between the blood access site and the artificial kidney.

Many of the tubing sets used in medical procedures involving extracorporeal treatment of fluid, such as hemodialysis, are configured so that fluid can flow through the system in a desired direction during the medical procedure. A pumping device can be used to control the fluid flow rate in the system. In hemodialysis, for example, a peristaltic pump is typically used to draw blood from the patient and move the blood through the tubing set during the treatment procedure. During hemodialysis, blood is initially drawn from the patient's blood access (e.g., a vein or an artery, but more typically an arteriovenous graft or fistula) and flows through a series of connected tubing segments to the artificial kidney for cleansing. After passing through the artificial kidney, the blood then flows through other tubing segments that return the blood to the patient. Thus there is generally a continuous circuit of blood flowing from the patient, through the artificial kidney, and then back to the patient during treatment.

During hemodialysis, blood is generally drawn from an upstream position in the blood access and then returned to a downstream position in the blood access. However, it has been found to be advantageous, for limited time periods, to reverse the direction that blood is received from and returned to the patient during hemodialysis. When the blood flow is reversed, blood is initially drawn from a downstream position in the blood access. The blood then flows through tubing segments to the artificial kidney for treatment before it is returned to the upstream position in the blood access. Typically this procedure is carried out by trained clinical personnel, e.g., dialysis clinicians. When the blood flow is reversed, any of various parameters, such as blood access flow rate, can be measured or derived from measurements. The data can provide useful information about the patient's condition and the effectiveness of the treatment. For example, practitioners can use information gathered during periods of reversed blood flow to evaluate the condition of the blood access, to get advanced warning on other health problems, such as access restrictions, and to prescribe preventive measures, such as blood access revision or replacements, which are generally needed after a few years of continuous dialysis.

Anything which makes the blood reversal maneuver faster and more secure would be generally helpful to clinicians in mastering and flawlessly carrying out this important procedure.

SUMMARY

In one aspect of the invention, a blood flow reversal valve for extracorporeal blood lines includes a first valve portion defining first and second ports extending therethrough and a second valve portion defining first and second ports extending therethrough. The valve portions are rotatably secured to one another, and configured to be rotated into a first position in which the first ports are aligned with one another and the second ports are aligned with one another. The valve portions are constructed to produce an audible click upon being rotated into the first position.

In another aspect of the invention, a blood flow reversal valve for extracorporeal blood lines includes a first valve portion defining first and second ports extending therethrough and a second valve portion defining first and second ports extending therethrough. The valve portions are rotatably secured to one another, and configured to be rotated into a first position in which the first ports are aligned with one another and the second ports are aligned with one another. The valve portions are constructed to provide tactile feedback to a clinician when the clinician manually rotates the valve portions into the first position.

In a further aspect of the invention, a blood flow reversal valve for extracorporeal blood lines includes a first valve portion defining first and second ports extending therethrough and a second valve portion defining first and second ports extending therethrough. The first and second valve portions are rotatable relative to one another between a first engaged position and a second engaged position. Each of the first and second valve portions includes at least one alignment feature. The alignment features are arranged to align with one another when the valve portions are in one of the engaged positions.

Embodiments may include one or more of the following features.

In some embodiments, the second valve portion includes a detent mechanism, and the first valve portion includes a projection configured to engage the detent when the valve portions are in the first position.

In certain embodiments, the detent mechanism includes two raised members that are circumferentially spaced from one another, and the projection is adapted to fit securely between the raised members when the valve portions are in the first position.

In some embodiments, one of the raised members includes a stop configured to prevent the first and second valve portions from being rotated relative to one another beyond a predetermined position.

In certain embodiments, the raised members extend from a side surface of the second valve portion.

In some embodiments, the projection extends from an inner surface of the first valve portion.

In certain embodiments, the projection is configured to snap into engagement with the detent mechanism when the first and second valve portions are rotated into the first position.

In some embodiments, the snapping of the projection into engagement with the detent mechanism produces the audible click.

In certain embodiments, the valve portions are constructed to provide tactile feedback to a clinician when the clinician manually rotates the valve portions into the first position.

In some embodiments, the valve portions are constructed to be substantially rotationally fixed relative to one another in the first position.

In certain embodiments, the first and second valve portions are configured to be rotated into a second position in which the first port of the first valve portion is aligned with the second port of the second valve portion and the second port of the first valve portion is aligned with the first port of the second valve portion.

In some embodiments, the second valve portion includes first and second detent mechanisms that are circumferentially spaced from one another by approximately 180 degrees.

In certain embodiments, the first valve portion includes a projection configured to engage the first detent mechanism when the valve portions are in the first position and configured to engage the second detent mechanism when the valve portions are in the second position.

In some embodiments, the valve portions are constructed to be substantially rotationally fixed relative to one another in the first and second positions.

In certain embodiments, the first and second valve portions are substantially disk-shaped, and coaxially rotatably connected to each other.

In some embodiments, the first and second valve portions are rotatable to a third position in which none of the ports are aligned with one another.

In certain embodiments, in the third position, blood is substantially prevented from passing from the first valve portion to the second valve portion.

In some embodiments, each of the valve portions includes an alignment feature, and the alignment features are arranged to align with one another when the valve portions are in the first position.

In certain embodiments, the first and second valve portions include blood line connectors configured to fluidly connect blood lines to the first and second valve portions, and the alignment features are disposed on the blood line connectors.

In some embodiments, the alignment features include bands adapted to be secured to the blood line connectors.

In certain embodiments, the blood flow reversal valve includes a gasket configured to be compressed between the first and second valve portions.

In some embodiments, the gasket is securable to one of the valve portions.

In certain embodiments, the tactile feedback includes increased rotational resistance.

In some embodiments, the valve is configured to produce increased rotational resistance over a span of about 15° to about 30°.

In certain embodiments, the tactile feedback includes an abrupt stop in rotation of the first and second valve portions relative to one another.

In some embodiments, the first valve portion includes a detent mechanism, and the second valve portion includes a projection configured to engage the detent mechanism when the valve portions are in the first position.

In certain embodiments, the detent mechanism includes a raised member constructed to provide rotational resistance to the valve portions.

In some embodiments, the raised member is configured to deflect the projection when the valve portions are rotated into the first position.

In certain embodiments, the alignment features include visual indicators.

In some embodiments, each of the valve portions includes first and second alignment features, and the first alignment features are dissimilar to the second alignment features.

In certain embodiments, the first alignment features are aligned with one another in the first position.

In some embodiments, the first alignment feature of the first valve portion is aligned with the second alignment feature of the second valve portion when the valve portions are in the second position.

In certain embodiments, the first and second valve portions include blood line connectors extending from outer surfaces of the valve portions, and the alignment features include visual indicators disposed on the blood line connectors.

In some embodiments, the alignment features include colored bands.

Embodiments may include one or more of the following advantages.

In some embodiments, the first and second valve portions are constructed to produce an audible click and/or tactile feedback when they are rotated relative to one another into a first position (e.g., a standard flow position) and/or a second position (e.g., a reversed flow position). The audible click and/or the tactile feedback can help to inform the clinician when the valve portions have been moved into the first position and/or the second position.

In certain embodiments, the blood line connectors include alignment features (e.g., visual indicators, such as colored bands). The alignment features can, for example, help to inform the clinician whether the valve is in the first position, the second position, or an intermediate position in between the first and second positions.

In some embodiments, the valve portions are configured to become rotationally fixed relative to one another when the valve is in the first and/or the second position. This rotationally fixed arrangement can help to prevent unintentional rotation of the valve portions relative to one another during treatment.

Other aspects, features, and advantages will be apparent from the description and drawings, and from the claims.

DESCRIPTION OF DRAWINGS

Like reference numerals in the various drawings indicate like elements.

DETAILED DESCRIPTION

Figure 1:
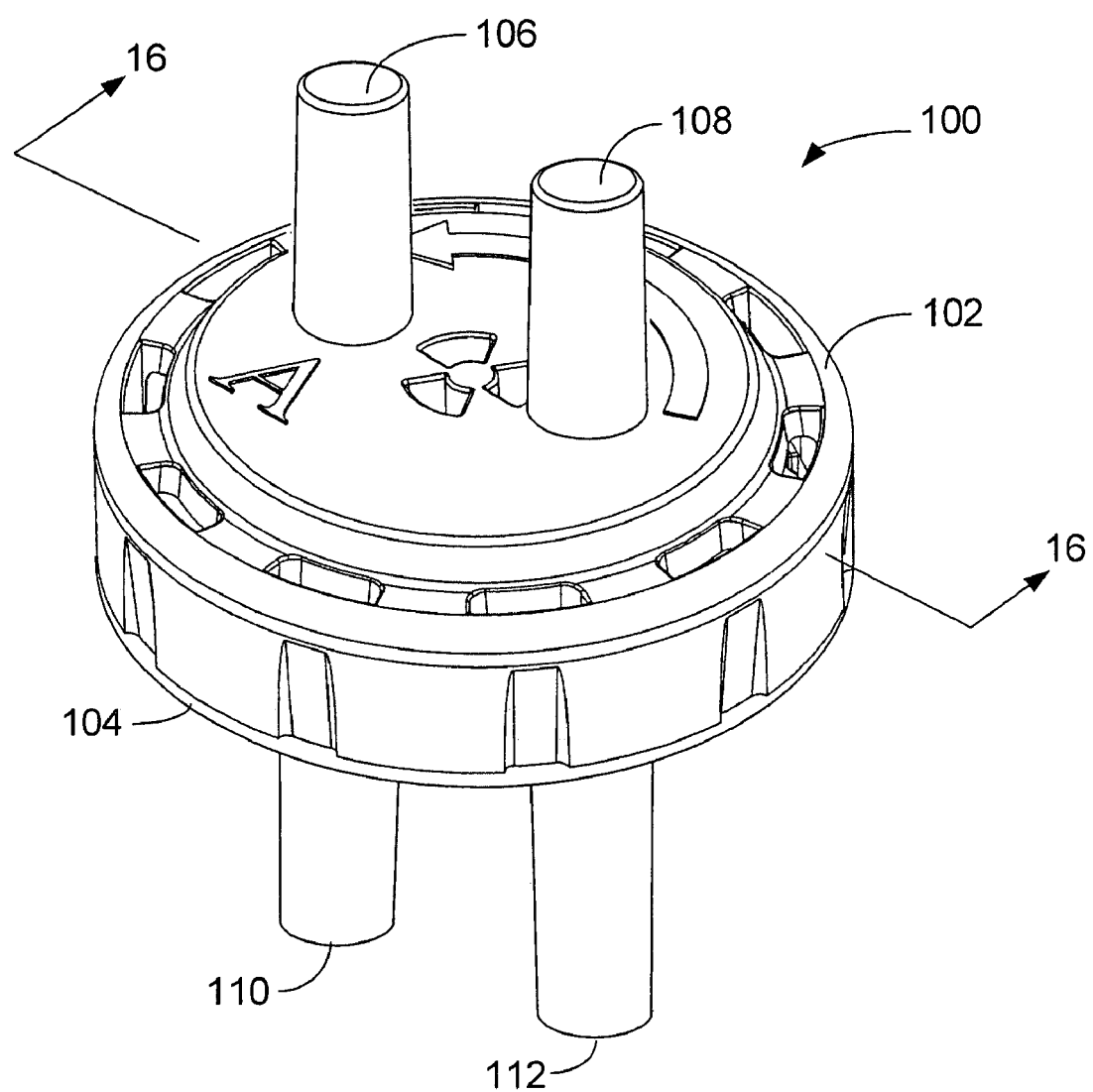
FIG. 1 is a perspective view of an embodiment of a blood flow reversal valve.
Figure 2:
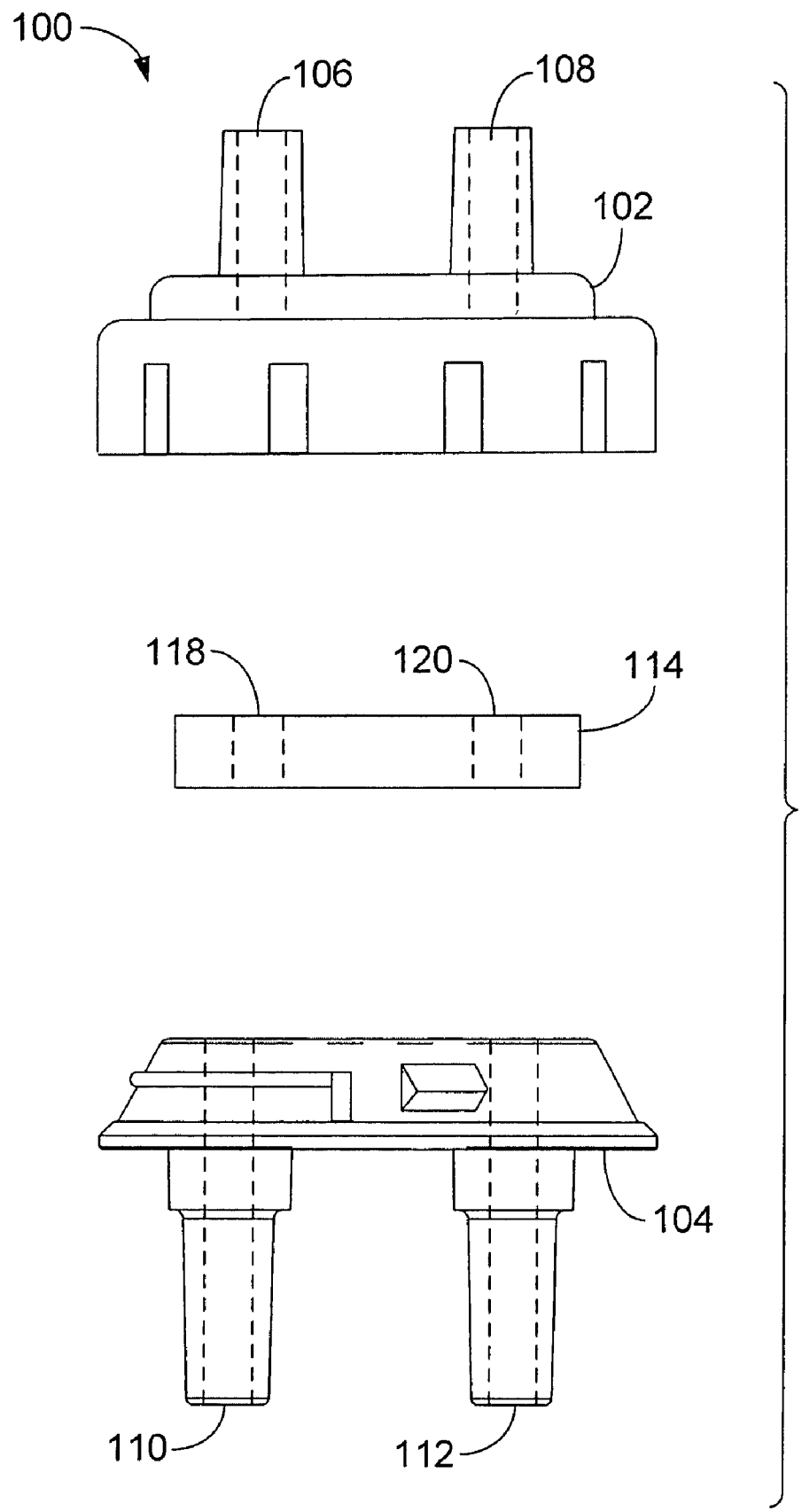
FIG. 2 is an axially exploded side view of the blood flow reversal valve of FIG. 1, showing its internal gasket as well as its top and bottom valve bodies.
Figure 3:
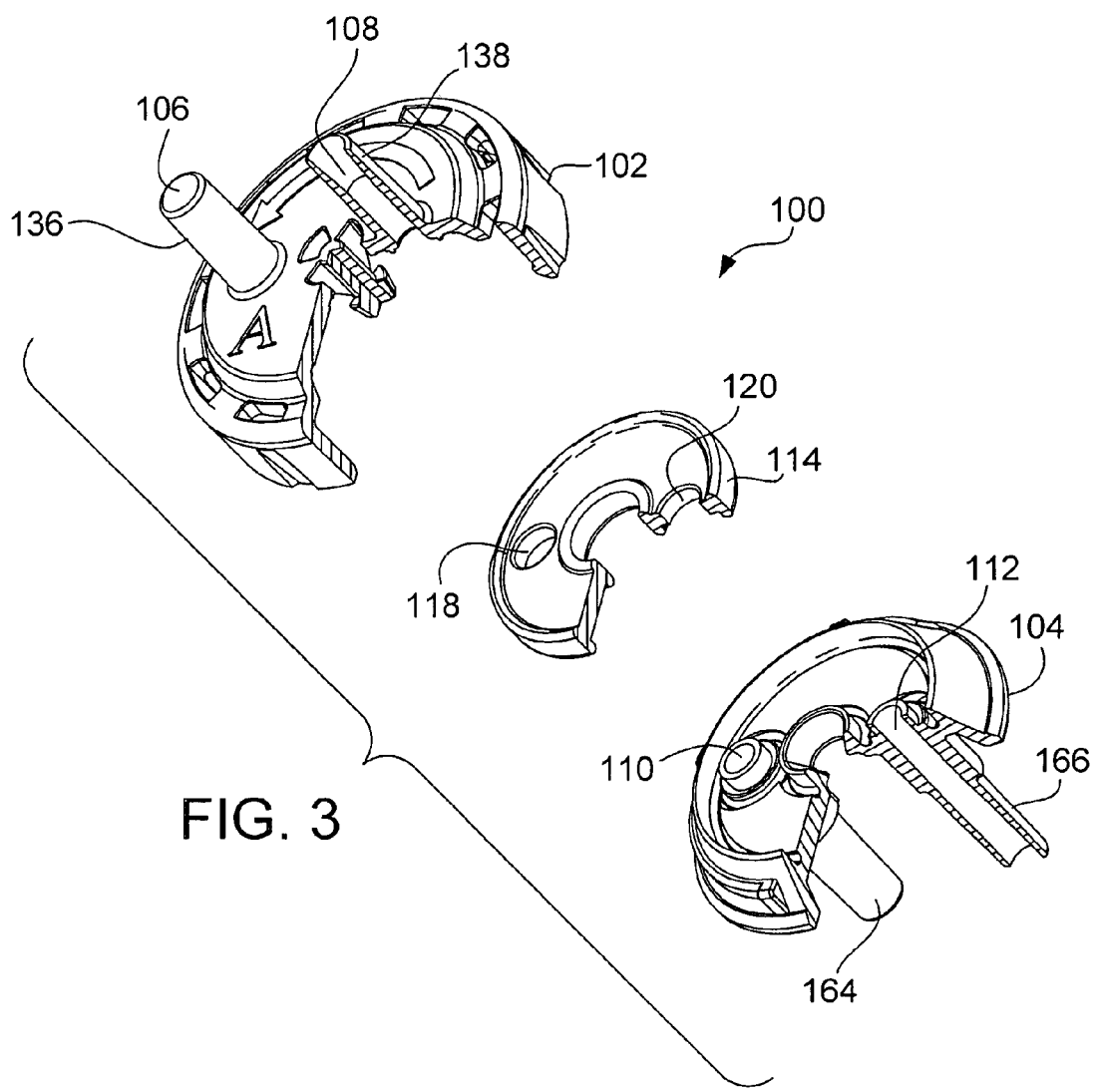
FIG. 3 is an axially exploded, perspective view of the blood flow reversal valve of FIG. 1, with portions cut away.

Referring to FIGS. 1-3, a blood flow reversal valve 100 includes a generally cylindrical top valve body 102, a generally cylindrical bottom valve body 104, and a generally disk-shaped gasket 114 situated between top valve body 102 and bottom valve body 104. Top valve body 102 includes two fluid passages 106 and 108 extending therethrough, and bottom valve body 104 includes two fluid passages 110 and 112 extending therethrough. Gasket 114 similarly includes two ports 118 and 120 extending therethrough. Passages 106, 118 and 110 are normally aligned, as are passages 108, 120 and 112 as shown in FIG. 2. Gasket 114, as described below, can be secured to bottom valve body 104 so that ports 118 and 120 of gasket 114 remain aligned with fluid passages 110 and 112 of bottom valve body 104, respectively, during use. Top valve body 102 and bottom valve body 104 are generally injection molded components preferably made of a biocompatible high-impact thermoplastic materials. Gasket 114 is generally a compression molded component made of silicone-like material as described in more detail below.

Top valve body 102 and bottom valve body 104 are coaxially rotatably secured to one another. Top valve body 102 and bottom valve body 104 can, for example, be rotated relative to one another into a first position in which fluid passage 106 is aligned with fluid passage 110 and fluid passage 108 is aligned with fluid passage 112, as shown in FIGS. 1 and 2. Top valve body 102 and bottom valve body 104 can also be rotated, preferably up to 180 degrees into other relative positions. In particular, top valve body 102 and bottom valve body 104 can be rotated relative to one another into an alternative, second position in which the alignment is reversed so that fluid passage 106 is aligned with fluid passage 112 and fluid passage 108 is aligned with fluid passage 110.

Blood flow reversal valve 100 is constructed to produce an audible click and tactile feedback when rotated into the first and second positions, which correspond to normal and reverse flow. Valve 100, as described below, also includes alignment features (e.g., visual indicators) that can help the clinician determine the rotational position of top valve body 102 and bottom valve body 104 relative to one another during use. The audible click, the tactile feedback, and the alignment features of valve 100 can, for example, help the clinician determine whether valve 100 is arranged in the first position, in the second position, or in an intermediate position between the first and second positions.

Valve 100, as described in more detail below, can be used as a component of the extracorporeal circuit of a blood treatment system (e.g., a hemodialysis system). During treatment, the route of blood flowing through fluid passages 106 and 108 of top valve body 102 can be switched by changing the position of top valve body 102 and bottom valve body 104 relative to one another. The direction in which blood enters and exits valve top valve body 102 can be reversed by rotating valve 100 from the first position in which fluid passage 106 is aligned with fluid passage 110 and fluid passage 108 is aligned with fluid passage 112 to the second position in which passage 106 is aligned with passage 112 and passage 108 is aligned with passage 110. Reversal of the blood flow can, for example, help the clinician take measurements to determine the flow rate of blood through the blood access.

Figure 4:
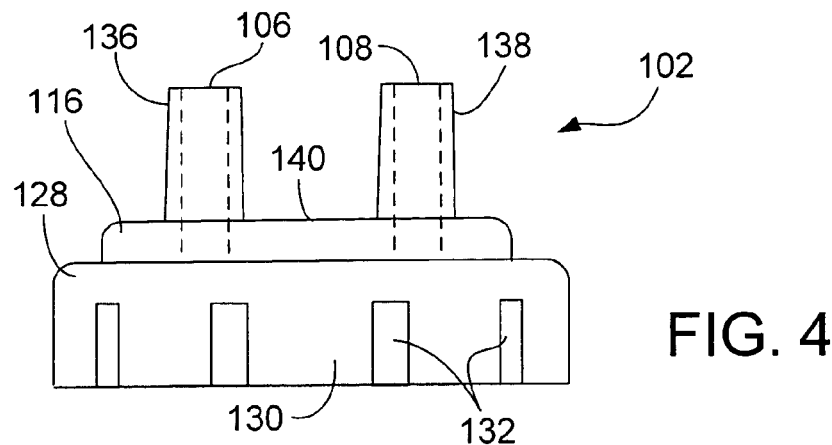
FIG. 4 is a side view of the top valve body of the blood flow reversal valve of FIGS. 1-3.
Figure 5:
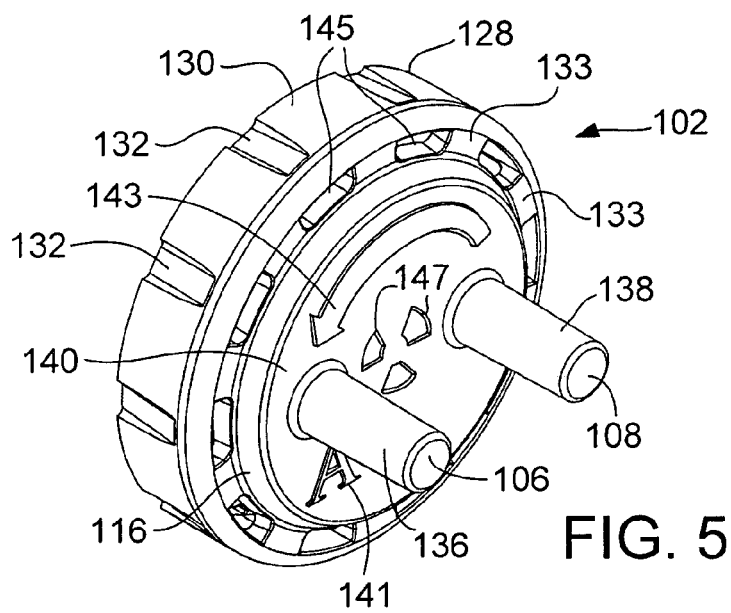
FIG. 5 is a top, perspective view of the top valve body of FIG. 4.

Referring to FIGS. 4 and 5, top valve body 102 is a generally cap-shaped device that includes a disk-shaped plate 116 and a cylindrical side wall 128 extending integrally from plate 116. Multiple circumferentially spaced connectors 133 extend inwardly from side wall 128 and connect side wall 128 to plate 116. Tubular blood line connectors 136 and 138 extend integrally from the outer surface 140 of plate 116 of top valve body 102. Plate 116 and blood line connectors 136 and 138 together form fluid passages 106 and 108, which extend from the outer end surfaces of blood line connectors 136 and 138 to an inner surface 124 (FIG. 6) of top valve body 102. Fluid passages 106 and 108 fluidly connect the exterior of top valve body 102 to the interior of top valve body 102. As a result, during use, blood can pass from the exterior of top valve body 102 to the interior of top valve body 102, and vice versa.

Side wall 128 generally extends around the circumference of plate 116. Side wall 128 and inner surface 124 form a cavity in which a seat portion of bottom valve body 104 can be secured when valve 100 is assembled, as described below.

As shown in FIG. 5, multiple outer apertures 145 are circumferentially spaced about the perimeter of top valve body 102 between connectors 133. Multiple center apertures 147 are circumferentially spaced about the perimeter of center pin 122. An exterior surface 130 of side wall 128 includes multiple grooves or depressions 132. Grooves 132 can provide improved grip for the clinician to rotate top valve body 102 relative to bottom valve body 104 during use. Other gripping mechanisms, such as ribs, knurls, and/or tabs, can alternatively or additionally be used to enhance the manual rotatability of top valve body 102.

Figure 6:
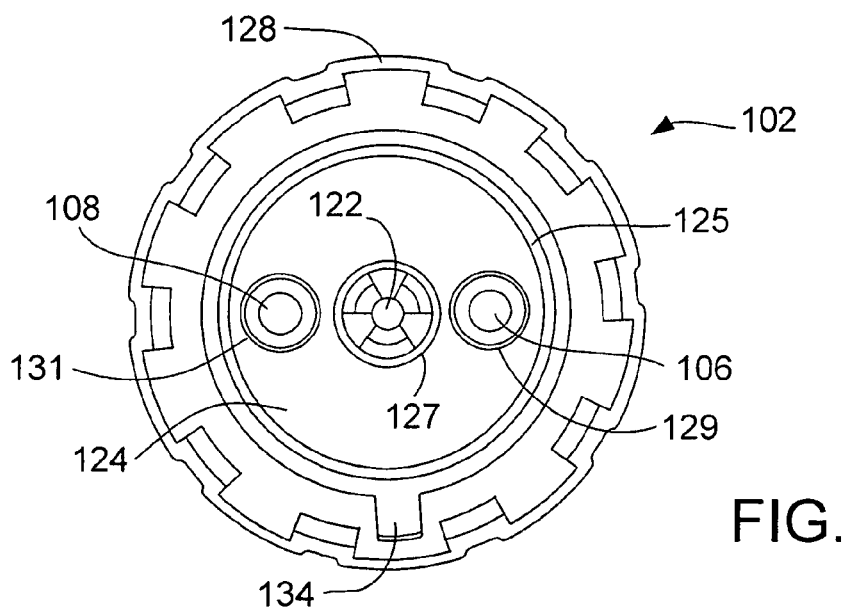
FIG. 6 is a bottom view of the top valve body of FIG. 4.

As shown in FIG. 6, fluid passages 106 and 108 are circumferentially spaced by about 180° and are positioned equidistant from the center of top valve body 102. Fluid passages 106 and 108 typically have a diameter of about 3.0 millimeters to about 3.8 millimeters. However, fluid passages can have larger or smaller diameters. Fluid passages 106 and 108 can, for example, have diameters ranging from about 1.5 millimeters to about 6.35 millimeters. In some embodiments, the diameters of fluid passages 106 and 108 gradually increase toward the distal end surfaces of blood line connectors 136 and 138. This gradual increase in diameter can help to prevent bubbles from developing in the blood as the blood enters and/or exits blood line connectors 136 and 138.

Figure 7:
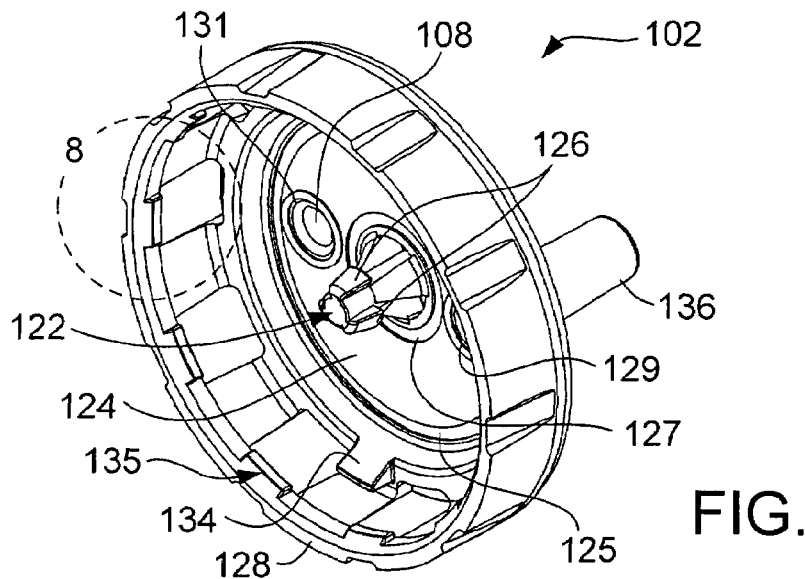
FIG. 7 is a bottom, perspective view of the top valve body of FIG. 4.
Figure 8:
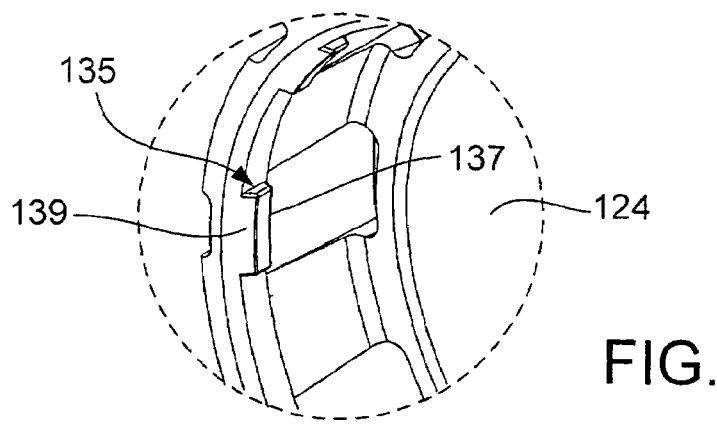
FIG. 8 is an enlarged detail view of the region 8 in FIG. 7.

Referring to FIG. 7, multiple resilient retaining members (e.g., resilient wedges) 135 extend inwardly (e.g., toward the center of top valve body 102) from side wall 128. Retaining members 135 are circumferentially spaced around side wall 128. As shown in FIG. 8, retaining members 135 include engagement surfaces 137 that extend substantially perpendicular to side wall 128, and guide surfaces 139 that extend at an acute angle relative to side wall 128. Retaining members 135, as described below, help to secure the seat portion of bottom valve body 104 within the cavity of top valve body 102.

Referring again to FIGS. 6 and 7, center pin 122 extends from the center of inner surface 124 of top valve body 102. Center pin 122 extends approximately along the rotational axis of top valve body 102. Multiple resilient fingers 126 are spaced about the circumference of center pin 122 at its free end. Resilient fingers 126 can be elastically deformed inwardly (e.g., toward the center of center pin 122) when an inward compressive force is applied to center pin 122. Like retaining members 135, center pin 122 cooperates with surfaces of bottom valve body 104 to secure top valve body 102 and bottom valve body 104 together.

As shown best in FIGS. 6 and 7, a resilient projection 134, designed to interact with cam-like surfaces on the bottom valve body during rotation, protrudes from inner surface 124 of top valve body 102 at a location that is spaced inwardly from side wall 128 and circumferentially about half way between the location of the two passages 106 and 108 situated between two of the resilient retaining members 135. Resilient projection 134 is constructed to elastically deform outwardly (e.g., toward side wall 128) when an outward force that exceeds a predetermined limit is applied to it, and is designed to snap back into its original position upon removal of the outward force. Resilient projection 134, as shown in FIG. 7, is substantially wedge-shaped and has generally flat circumferential end surfaces. Resilient projection 134 can cooperate with one or more structural features of bottom valve body 104 to prevent top valve body 102 and bottom valve body 104 from rotating relative to one another beyond a predetermined position. The inner surface of resilient projection 134 generally extends at an acute angle relative to side wall 128.

Annular channels 125 and 127 are formed in inner surface 124 as shown in FIGS. 6 and 7. Channel 125 extends generally around the perimeter of plate 116, and channel 127 extends around the perimeter of center pin 122. These channels can be configured to receive raised annular edges or rims of gasket 114 when valve 100 is assembled, which insures a fluid tight seal between top valve body 102 and gasket 114 during use. Annular rims 129 and 131 extend from inner surface 124 around fluid passages 106 and 108, respectively. Annular rims 129 and 131 also help to promote a fluid-tight seal between top valve body 102 and gasket 114 while top valve body 102 is being rotated relative to bottom valve body 104 and gasket 114 and while top valve body 102 is stationary relative to bottom valve body 104 and gasket 114.

Figure 9:
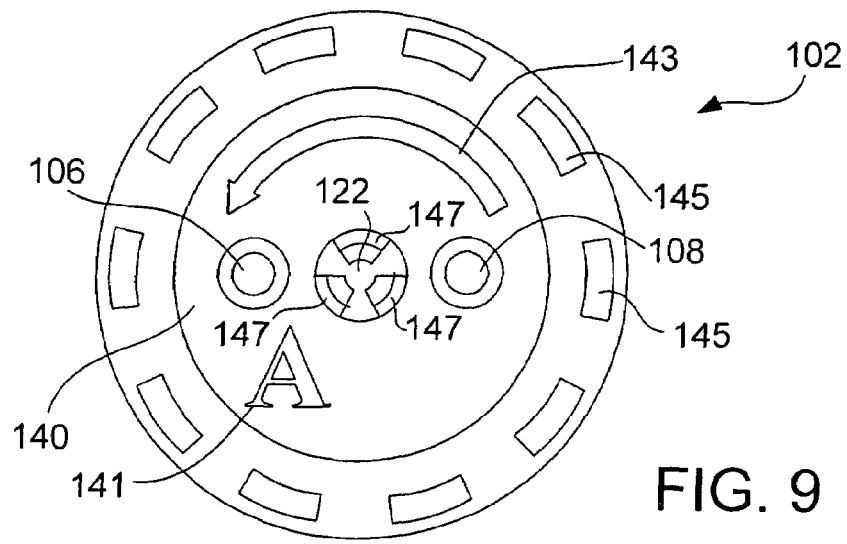
FIG. 9 is a top view of the top valve body of FIG. 4.

Top valve body 102 also includes alignment features, which can help the clinician to operate valve 100 in accordance with the methods described herein, and, in addition, serve as an aid in assembling the valve. Referring to FIG. 9, for example, outer surface 140 of top valve body 102 includes a letter 141 and an arrow 143. Letter 141 and/or arrow 143 can be raised relative to outer surface 140. As a result, letter 141 and arrow 143 can provide the clinician with tactile reference points as well as visual reference points during use. Letter 141 and arrow 143 is preferably integrally molded but can be formed on top valve body 102 using any of various techniques, such as molding, printing, pressing, and/or stamping. Letter 141 and arrow 143 can help the clinician to position top valve body 102 as desired relative to bottom valve body 104 during use. Letter 141 can, for example, help the clinician to initially align top valve body 102 and bottom valve body 104 during assembly, and arrow 143 can help indicate to the clinician the direction in which top valve body 102 can be rotated relative to bottom valve body 104 in order to move valve 100 from the first position to the second position.

Top valve body 102 is preferably formed of biocompatible injection molded acrylic-based multipolymer compound (e.g., a biocompatible high impact MMA/styrene/acrylonitrile terpolymer or similar injection moldable thermoplastic compound). However, in some embodiments, one or more other materials and/or manufacturing techniques can be used. In certain embodiments, top valve body 102 and bottom valve body 104 may be formed of one or more biocompatible thermoplastic or thermoset materials. In some embodiments, top valve body 102 may include one or more relatively rigid materials. In certain embodiments, top valve body 102 may include one or more relatively resilient materials. Top valve body 102 can, for example, include acrylic-based multipolymers, polycarbonate, polysulfone, or blends of these types of materials.

Figure 10:
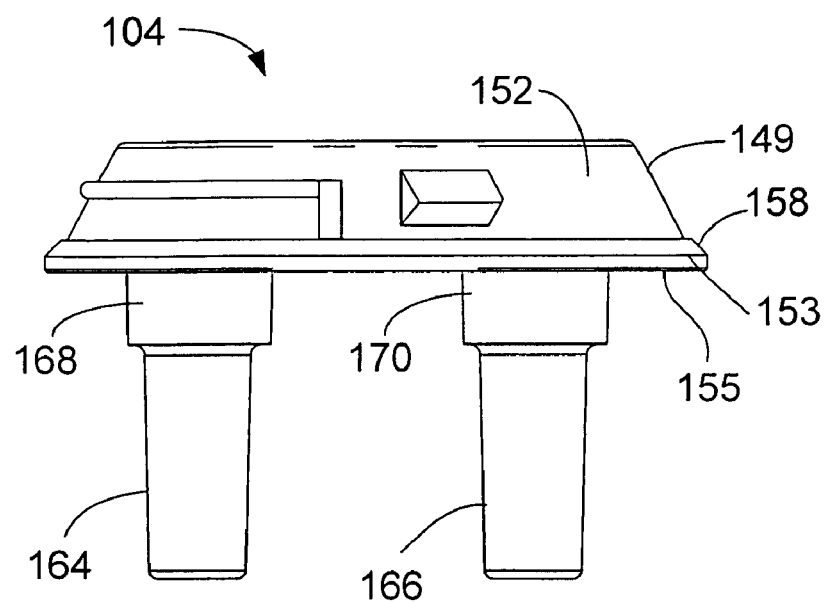
FIG. 10 is a side view of the bottom valve body of the blood flow reversal valve of FIGS. 1-3.
Figure 11:
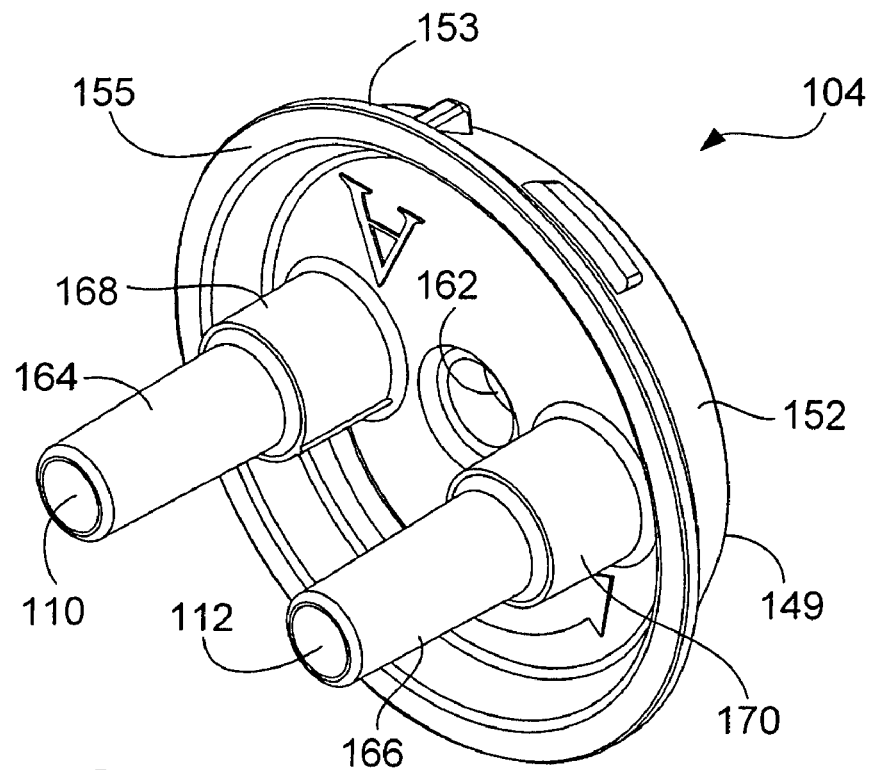
FIG. 11 is a bottom, perspective view of the bottom valve body of FIG. 10.

Referring to FIGS. 10 and 11, bottom valve body 104, like top valve body 102, is a substantially disk-shaped device. Bottom valve body 104 includes a tapered seat 149, which has a slightly smaller diameter than the cavity formed by side wall 128 and inner surface 124 of top valve body 102. Consequently, seat 149 can be inserted into the cavity formed by top valve body 102. Generally, when seat 149 is inserted into the cavity of top valve body 102, as shown in FIG. 1, for example, sufficient space remains between a side surface 152 of seat 149 and side wall 128 of top valve body 102 (FIGS. 4-7) to allow top valve body 102 and bottom valve body 104 to rotate relative to one another. For example, a clearance of about 0.127 millimeter can exist between seat 149 and side wall 128.

Tubular blood line connectors 164 and 166 extend from an outer surface 144 of bottom valve body 104. Blood line connectors 164 and 166 include base portions 168 and 170, respectively, which have a larger outer diameter than the remainder of the blood line connectors. Base portions 168 and 170 can provide blood line connectors 164 and 166 with increased mechanical strength, which can help to prevent shearing of the blood line connectors 164 and 166 as the clinician rotates bottom valve body 104 relative to top valve body 102. Blood line connectors 164 and 166, together with seat 149, form fluid passages 110 and 112, which fluidly connect the interior of bottom valve body 104 to the exterior of bottom valve body 104. Fluid passages 110 and 112 are circumferentially spaced by about 180° and are positioned equidistant from the center of bottom valve body 104. Fluid passages 110 and 112 of bottom valve body 104 and fluid passages 106 and 108 of top valve body 102 preferably have substantially similar dimensions (e.g., substantially similar diameters). The similar dimensions of the fluid passages help to prevent turbulent blood flow as blood passes through valve 100, from top valve body 102 to bottom valve body 104 and vice versa. This can help to prevent blood conditions, such as hemolysis, from occurring during use of valve 100.

As shown in FIG. 10, flange 153 extends circumferentially around an outer edge of seat 149. Flange 153 includes an outer surface 155 and a tapered surface 158. When top valve body 102 and bottom valve body 104 are assembled, retaining members 135 (e.g., engagement surfaces 137 of retaining members 135) (FIG. 8) engage outer surface 155 of flange 153 to trap the bottom valve body as it snaps in place and thus prevent top valve body 102 and valve 104 from being separated from one another.

Figure 12:
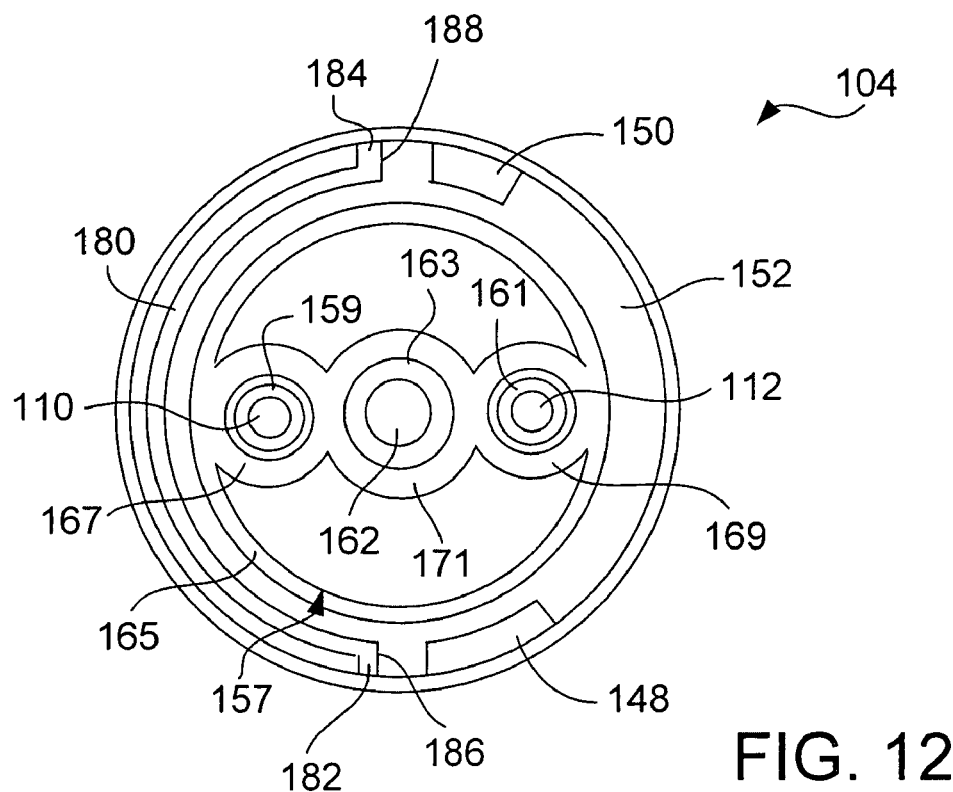
FIG. 12 is a top view of the bottom valve body of FIG. 10.
Figure 13:
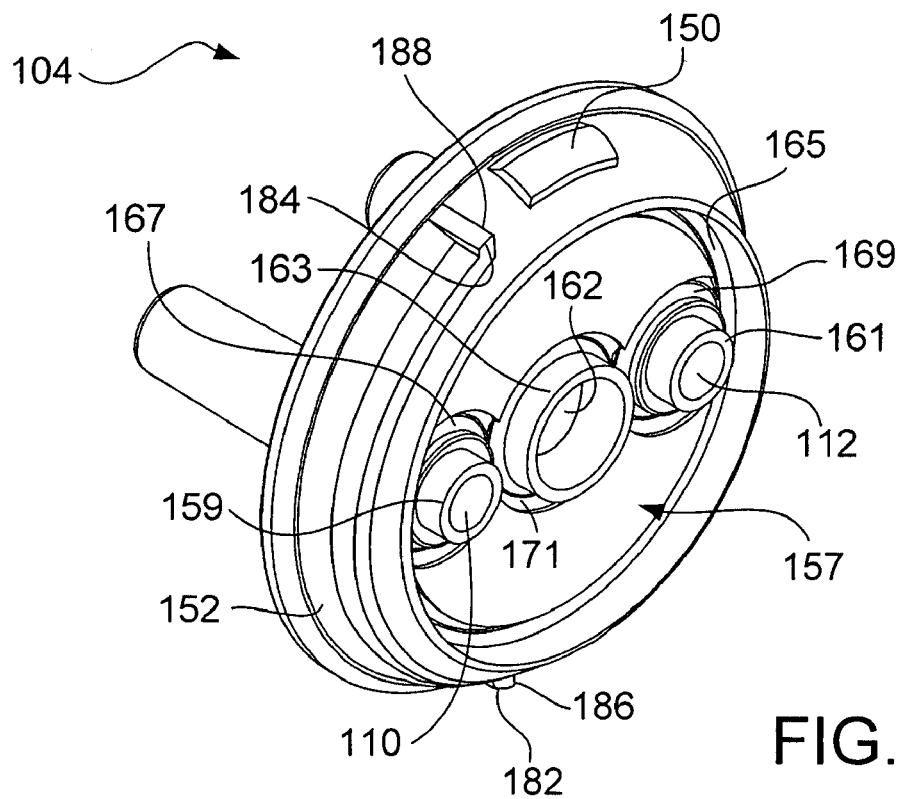
FIG. 13 is a top, perspective view of the bottom valve body FIG. 10.

Referring to FIGS. 12 and 13, a cylindrical passage 162 extends through the center of seat 149. Passage 162 has a diameter that is slightly less than (e.g., about 0.51 millimeter to about 0.61 millimeter less than) the diameter of center pin 122 of top valve body 102 (FIGS. 6 and 7). Passage 162 can be configured to receive center pin 122 of top valve body 102 when valve 100 is assembled to help secure top and bottom valve bodies 102 and 104 together.

Still referring to FIGS. 12 and 13, the inner surface of bottom valve body 104 includes a recessed region 157. Recessed region 157 is sized and shaped to receive gasket 114. Tubular members 159 and 161 extend from the surface of recessed region 157 around fluid passages 110 and 112. A tubular member 163 similarly extends from the surface of recessed region 157 around the perimeter of passage 162. Multiple annular channels 165, 167, 169, and 171 are formed in the surface of recessed region 157. Annular channel 165 extends around the circumference of recessed region 157. Annular channels 167, 169, and 171 extend around the perimeters of tubular members 159, 161, and 163, respectively. Annular channels 165, 167, 169, and 171 are sized and shaped to receive raised features (e.g., raised ridges) 173, 175, 177, and 179, respectively, of gasket 114 (FIG. 15A) when valve 100 is assembled. The mating relationship between the channels of valve body 104 and the raised features of gasket 114 insure a relatively fluid tight seal between those components.

A semi-circular ridge 180 extends from tapered side surface 152 of seat 149 and is integrally attached to stops 182 and 184 at its circumferential ends. Stops 182 and 184 are raised members that extend outwardly from side surface 152. End surfaces 186 and 188 of stops 182 and 184, respectively, can, for example, extend at an angle that is substantially perpendicular to side surface 152. Semi-circular ridge 180 reinforces stops 182 and 184. Thus, semi-circular ridge 180 can help to prevent stops 182 and 184 from being deformed when a rotational force is applied to stops 182 and 184.

Two locking features (e.g., raised bars) 148 and 150 also extend from side surface 152 of seat 149. Locking features 148 and 150 can, for example, extend about 0.4 millimeter to about 0.5 millimeter outwardly from side surface 152. Locking features 148 and 150 are generally circumferentially spaced from stops 182 and 184, respectively, by a distance that is slightly greater than or equal to the circumferential length of projection 134 (FIGS. 6 and 7). Locking features 148 and 150 can, for example, be circumferentially spaced apart from stops 182 and 184, respectively, by about 10 degrees to about 15 degrees (e.g., about 12.5 degrees to about 13.5 degrees). Locking features 148 and 150 can be circumferentially spaced from stops 182 and 184, respectively, by about 2.0 millimeters to about 5.0 millimeters (e.g., about 3.63 millimeters to about 3.70 millimeters). Stops 182 and 184 can extend outwardly from side surface 152 by about 2.0 millimeter or more (e.g., about 3.0 millimeters or more, 4.0 millimeters or more) and/or about 5.0 millimeters or less (e.g., about 4.0 millimeters or less, about 3.0 millimeters or less).

Figure 14:
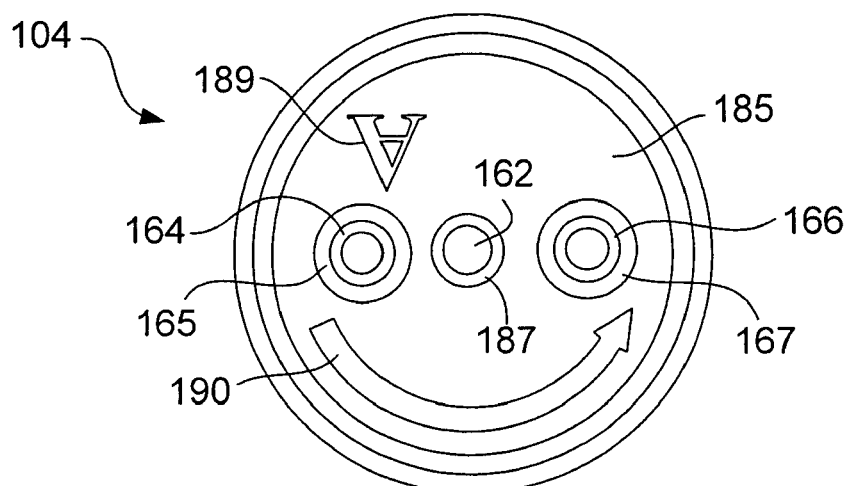
FIG. 14 is a bottom view of the bottom valve body of FIG. 10.

As shown in FIG. 14, an outer surface 185 of bottom valve body 104 includes an annular depression 187 extending around passage 162. Annular depression 187 provides a flanged surface that can be engaged by resilient fingers 126 of center pin 122 (FIG. 7) when valve 100 is assembled. The engagement of resilient fingers 126 with the flanged portion of outer surface 185 can help to secure top valve body 102 and bottom valve body 104 to one another. Outer surface 185 also includes a letter 189 and an arrow 190. Letter 189 and arrow 190 are similar to those discussed above with respect to top valve body 102. Letter 189 and arrow 190 can help the to initially align top valve body 102 and bottom valve body 104 during assembly and can help indicate to the clinician the direction in which bottom valve body 104 can be rotated relative to top valve body 102 in order to move valve 100 from the first, standard flow position to the second, reverse flow position. Letter 189 and arrow 190 can also be used together with letter 141 and arrow 143 on top valve body 102 to determine the rotational position of bottom valve body 104 relative to top valve body 102 (e.g., to determine whether valve 100 is in the first position, the second position, or an intermediate position between the first and second positions).

Bottom valve body 104, like top valve body 102, is generally formed of an injection molded thermoplastic, preferably an acrylic-based multipolymer (e.g., a biocompatible high impact MMA/styrene/acrylonitrile terpolymer or similar injection moldable thermoplastic compound). Bottom valve body 104, however, can alternatively or additionally be formed using any of the various other materials and/or techniques described above with respect to top valve body 102.

Figure 15A:
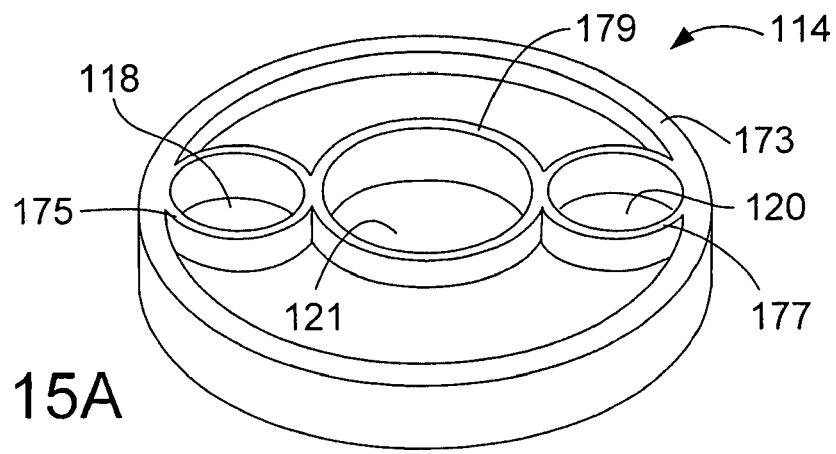
FIGS. 15A and 15B are, respectively top and bottom, perspective views of the gasket inside the blood flow reversal valve of FIGS. 1-3.
Figure 15B:
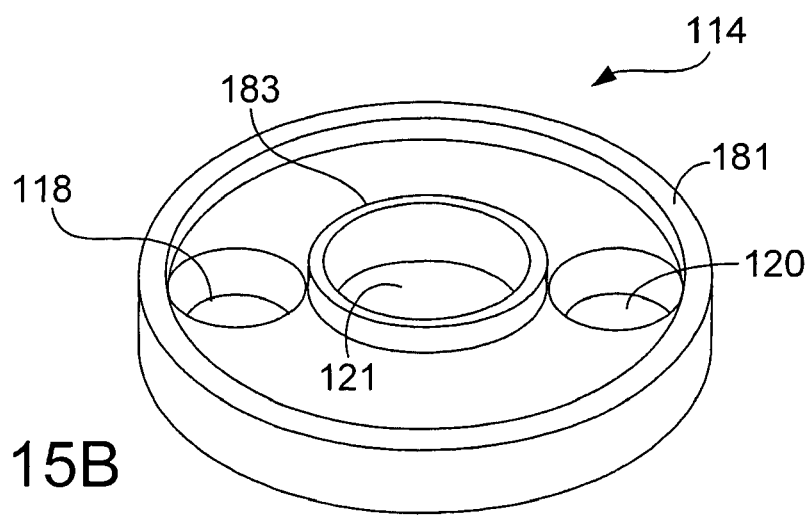

Referring to FIGS. 15A and 15B, gasket 114 includes fluid ports 118 and 120 and a central aperture 121. Ports 118 and 120 are circumferentially spaced by approximately 180° and are spaced equidistant from the center of gasket 114. Gasket 114 is generally sized and shaped to fit within recessed region 157 of bottom valve body 104 (FIGS. 12 and 13). A bottom side of gasket 114, as shown in FIG. 15A, includes multiple protruding ridges 173, 175, 177, and 179. Protruding ridge 173 extends around the perimeter of gasket 114. Ridges 175 and 177 extend around ports 118 and 120, and ridge 179 extends around central aperture 121. Gasket 114 can be secured within recessed region 157 of bottom valve body 104 such that ports 118 and 120 of gasket 114 are aligned with fluid passages 110 and 112, respectively, of bottom valve body 104. When positioned within recessed region 157 of bottom valve body 104, tubular members 159 and 161 of bottom valve body 104 extend at least partially through ports 118 and 120, and tubular member 163 of bottom valve body 104 extends at least partially through central aperture 121. Similarly, ridges 173, 175, 177, and 179 of gasket 114 extend into channels 165, 167, 169, and 171, respectively, formed in the inner surface of bottom valve body 104. As a result, gasket 114 can be substantially prevented from rotating relative to bottom valve body 104 during use. The interaction between the ridges of gasket 114 and the channels of bottom valve body 104 can also help to promote a fluid-tight seal between gasket 114 and bottom valve body 104.

As shown in FIG. 15B, an opposite side of gasket 114 also includes a protruding annular rim 181 extending about its perimeter and a raised annular surface 183 extending around aperture 121. When valve 100 is assembled, rim 181 and raised surface 183 of gasket 114 extend into channels 125 and 127, respectively, of top valve body 102 (FIGS. 6 and 7). The interaction of rim 181 with channel 125 and of raised surface 183 with channel 127 helps to promote a fluid-tight seal between gasket 114 and top valve body 102. Rim 181 and raised surface 183 can slide within channels 125 and 127, respectively, when top valve body 102 and bottom valve body 104 are rotated relative to one another.

Gasket 114 is generally more compliant than top valve body 102 and bottom valve body 104. In certain embodiments, gasket 114 has a thickness that is slightly greater than the distance between the inner surfaces of top valve body 102 and bottom valve body 104 when they are secured to one another. As a result, gasket 114 can be compressed between top valve body 102 and bottom valve body 104 when valve 100 is assembled, which can help to ensure a fluid tight seal of valve 100.

Gasket 114 is generally formed of polyisoprene using compression molding techniques. However, other materials and/or techniques can be used to form gasket 114. In certain embodiments, gasket 114 includes one or more biocompatible materials. In some embodiments, gasket 114 includes one or more relatively compliant materials. Gasket 114 can, for example, include one or more materials that have a durometer of about 30 Shore D to about 40 Shore D (e.g., about 30 Shore D). In certain embodiments, gasket 114 includes one or more thermoplastic elastomers. In some embodiments, gasket 114 includes latex, silicone, krayton, or blends of these types of materials.

To assemble valve 100, gasket 114 can first be positioned in bottom valve body 104, as described above, and then top valve body 102 and bottom valve body 104 can be snap fitted together. Seat 149 of bottom valve body 104 and gasket 114 can, for example, be inserted into the cavity of top valve body 102. While inserting seat 149 into the cavity of top valve body 102, blood line connectors 136 and 138 of top valve body 102 can be circumferentially spaced apart from blood lines 164 and 166 bottom valve body 104 by approximately 90 degrees. This spacing can help to insure that projection 134 of cover 102 (FIG. 7) is positioned within the space between locking features 148 and 150 of bottom valve body 104 (FIG. 12).

Figure 16:
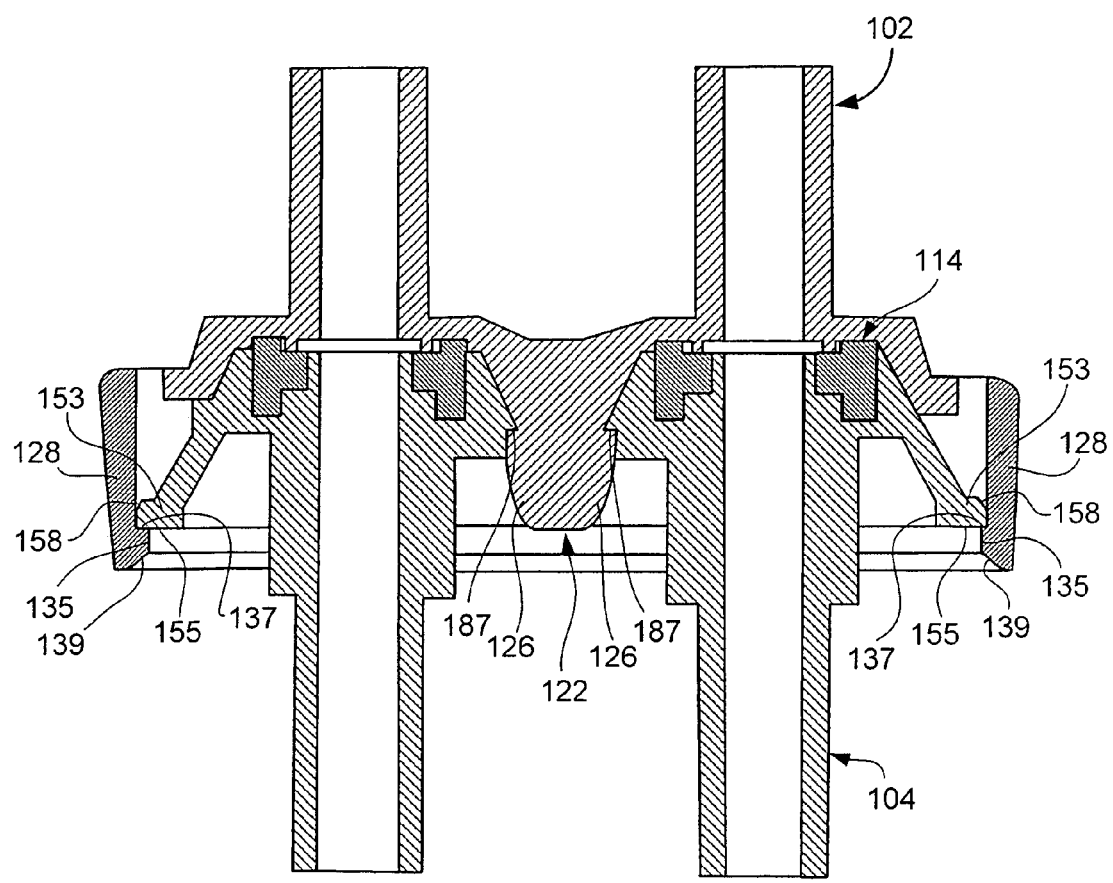
FIG. 16 is a cross-sectional view taken along line 16-16 in FIG. 1.

As shown in FIG. 16, when top valve body 102 and bottom valve body 104 are pressed together, retaining members 135 (e.g., engagement surfaces 137 of retaining members 135), which extend inwardly from side wall 128 of top valve body 102, engage flange 153 (e.g., outer surface 155 of flange 153), which extends around the perimeter of bottom valve body 104. As top valve body 102 and bottom valve body 104 are pressed together, guide surfaces 139 of retaining members 135 slide against tapered surface 158 of flange 153, causing retaining members 135 to deflect outward. As seat 149 of bottom valve body 104 becomes seated within the cavity of top valve body 102, engagement surfaces 137 of retaining members 135 snap into engagement with outer surface 155 of flange 153. The engagement of retaining members 135 and the outer surface of bottom valve body 104 provides a compressive force about the outer circumference of valve 100, which can help to secure top valve body 102 and 104 together and can help to promote a fluid tight seal between top valve body 102 and bottom valve body 104 by compressing gasket 114 between top valve body 102 and bottom valve body 104.

As seat 149 is inserted into the cavity of top valve body 102, center pin 122 of top valve body 102 penetrates cylindrical passage 162 of bottom valve body 104. An inward force is applied to center pin 122 by seat 149 of bottom valve body 104 as center pin 122 passes through cylindrical passage 162. This inward force deflects resilient fingers 126 of center pin 122 inwardly until the end region of center pin 122 has passed through cylindrical passage 162. After the end region of center pin 122 has passed through cylindrical passage 162, resilient fingers 126 expand outwardly to their original shape. Consequently, as shown in FIG. 16, resilient fingers 126 engage the flanged region of the outer surface of bottom valve body 104 formed by annular depression 187. This engagement can create a compressive force in the center region of valve 100, which can help to prevent top valve body 102 and bottom valve body 104 from becoming detached from one another. The compressive force can further help to ensure a fluid tight seal in the center region of valve 100 by compressing gasket 114 between top valve body 102 and bottom valve body 104.

By providing engagement around both the perimeter and at the central region of valve 100, the compressive forces acting on gasket 114 can be distributed more evenly across gasket 114.

When valve 100 is assembled, top valve body 102 and bottom valve body 104 can be rotated between first and second positions, which are circumferentially spaced by approximately 180°. To rotate top valve body 102 and bottom valve body 104 relative to one another, the clinician can grasp side wall 128 of top valve body 102 and rotate top valve body 102 while holding bottom valve body 104 in a fixed position (e.g., by grasping blood line connectors 164 and 166 of bottom valve body 104). Alternatively or additionally, the clinician can grasp the blood line connectors of both top valve body 102 and bottom valve body 104 to rotate top valve body 102 and bottom valve body 104 relative to one another.

Figure 17A:
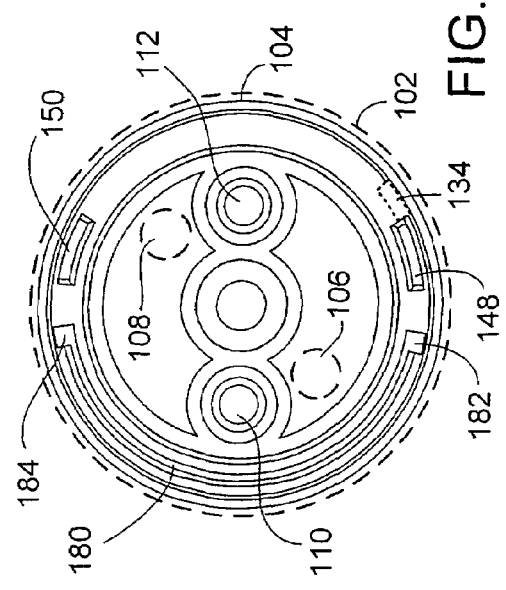
FIGS. 17A-17D are top, schematic views illustrating the operation of the blood flow reversal valve of FIG. 1, showing respective phases of relative rotation between the top and bottom valve bodies, features of the top valve body being shown in phantom.

Referring to FIG. 17A, after initial assembly of valve 100, projection 134 is positioned in an intermediate position between locking features 148 and 150 (e.g., between the first and second positions). The clinician can rotate top valve body 102 and bottom valve body 104 relative to one another in the clockwise direction in order to reposition valve 100 from this intermediate position to the first position. When projection 134 is positioned between locking features 148 and 150, top valve body 102 and bottom valve body 104 can rotate relatively freely relative to one another (e.g., with little resistance). A clearance of about 0.13 millimeter and 0.18 millimeter generally exists between projection 134 and side wall 152 of bottom valve body 104 when projection 134 is positioned in the zone between locking features 148 and 150. Consequently, projection 134 provides substantially no rotational resistance within this zone.

Figure 17B:
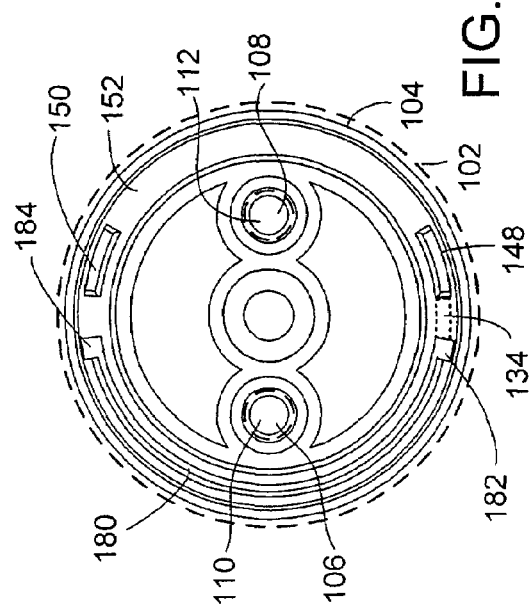

As shown in FIG. 17B, as top valve body 102 and bottom valve body 104 are rotated toward the first position, projection 134 contacts locking feature 148. The clinician generally feels a tactile sensation (e.g., increased rotational resistance) when projection 134 contacts locking feature 148.

Figure 17C:
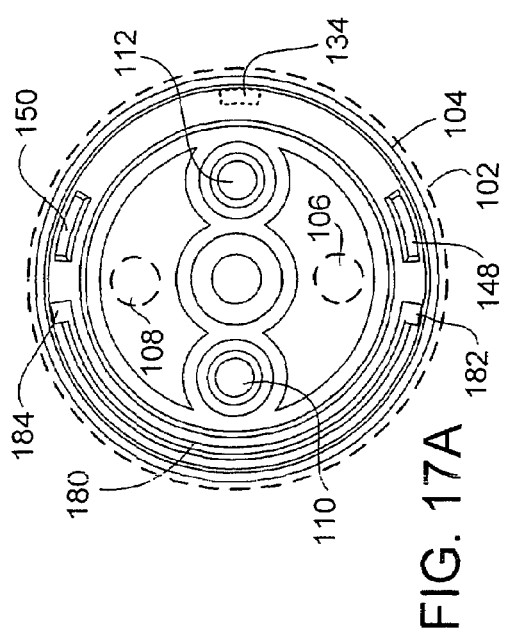

Referring to FIG. 17C, as the clinician continues to rotate top valve body 102 and bottom valve body 104 relative to one another, locking feature 148 deflects projection 134 outward as projection 134 slides along and rides over locking feature 148. As projection 134 slides over locking feature 148, the rotational resistance encountered by the clinician is at an increased level as compared to the level of resistance encountered when projection 134 is positioned in the low-resistance zone between locking features 148 and 150. The zone of increased resistance (e.g., the zone in which projection 134 rides over locking feature 148) can span about 15° to about 30° (e.g., about 22.5° to about 23.5°, about 23°). This increased resistance indicates to the clinician that projection 134 is in contact with locking feature 148. The increased resistance can, therefore, serve as tactile feedback to inform the clinician that top valve body 102 and bottom valve body 104 are adjacent and approaching the first position.

Figure 17D:
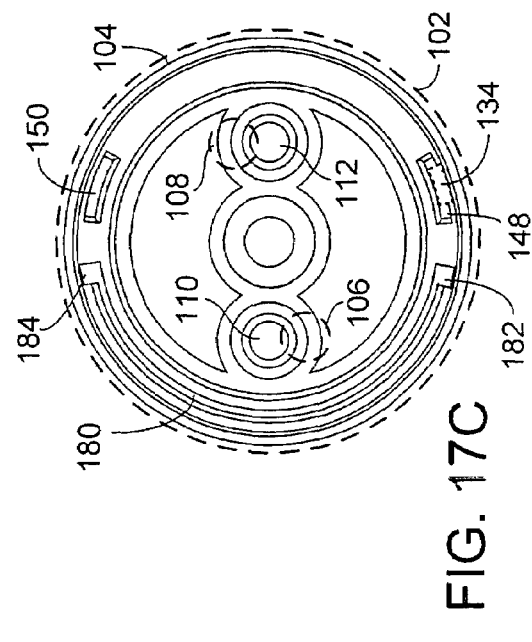

As shown in FIG. 17D, continued rotational force applied by the clinician can cause projection 134 to slide completely over locking feature 148 into the detent region formed between locking feature 148 and stop 182, where it becomes "trapped". Consequently, valve 100 becomes rotationally locked or fixed in the first position in which fluid passages 106 and 110 are aligned with one another and fluid passages 108 and 112 are aligned with one another. When rotated into the detent region between locking feature 148 and stop 182 (e.g., when rotated into the first position), projection 134 snaps inward as it slides off the locking feature 148, producing an audible click. For example, abrupt contact between projection 134 and side wall 152 of bottom valve body 104 can produce the audible click. Alternatively or additionally, the audible click can be produced by contact made between projection 134 and stop 182 as projection 134 is forcibly rotated into stop 182. The audible click produced by top valve body 102 and bottom valve body 104 as the projection 134 seats, serves to indicate to the clinician that valve 100 has been successfully rotated completely into the first position. The contact between projection 134 and side wall 152 and/or the contact between projection 134 and stop 182, can cause energy to be transmitted to the clinician (e.g., to the hand of the clinician) through top valve body 102 and/or bottom valve body 104. Consequently, in addition to the audible click, the clinician can experience a tactile sensation that can serve as an indication that top valve body 102 and bottom valve body 104 have reached the first position.

When valve 100 is in the first position, as shown in FIG. 17D, projection 134 abuts end surface 186 of stop 182. Consequently, top valve body 102 is prevented from rotating any further in the clockwise direction (as viewed from the top of top valve body 102). At its other end, projection 134 abuts locking feature 148. Locking feature 148 is constructed to retain projection 134 in the detent formed between locking feature 148 and stop 182 such that top valve body 102 and bottom valve body 104 are held in a substantially rotationally fixed position relative to one another. Projection 134 can, for example, be fixed between stop 182 and locking feature 148 until sufficient rotational force is applied to top valve body 102 and/or bottom valve body 104 to cause projection 134 to slide back over locking feature 148 toward the second position (e.g., toward locking feature 150 and stop 184).

In order to release top valve body 102 and bottom valve body 104 from the first position, the clinician can, by using sufficient force, rotate top valve body 102 in the counter clockwise direction (as viewed from the top of top valve body 102) relative to bottom valve body 104 such that projection 134 is rotated into and back over locking feature 148. The clinician can continue to rotate top valve body 102 and bottom valve body 104 relative to one another until reaching the second position in which projection 134 is seated in between locking feature 150 and stop 184. Rotation of valve 100 into the second position can produce an audible click and tactile feedback in the same manner as discussed above with respect to the first position.

Figure 18:
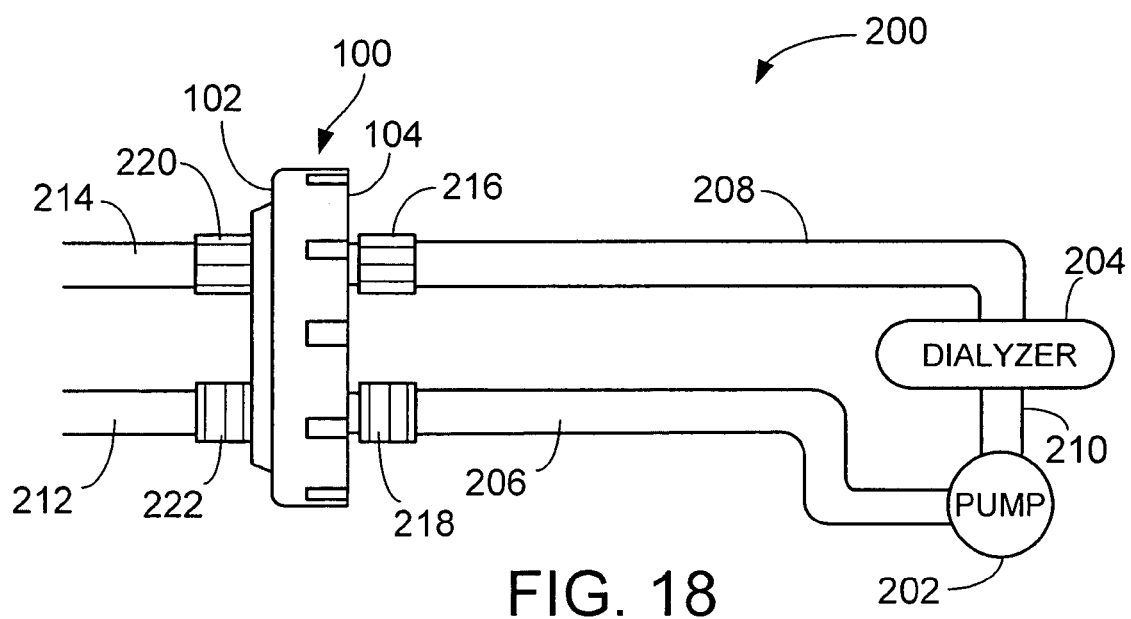
FIG. 18 is a schematic diagram of the blood flow reversal valve of FIG. 1 connected to an extracorporeal blood line for hemodialysis in an embodiment of a blood treatment system.

FIG. 18 illustrates an exemplary blood treatment system (e.g., a hemodialysis system) 200 that includes valve 100. Bottom valve body 104 of valve 100 is fluidly connected to a pump 202 via an outlet blood line 206. Bottom valve body 104 is fluidly connected to a blood treatment device (e.g., a dialyzer) 204 via an inlet blood line 208. Pump 202 is fluidly connected to blood treatment device 204 via a connection tube 210. On the opposite side of valve 100, arterial and venous blood lines 212 and 214 are fluidly connected to top valve body 102. At their opposite ends, arterial and venous blood lines 212 and 214 can be connected to a patient during treatment, as discussed below.

Outlet and inlet blood lines 206 and 208 can be secured to blood line connectors 164 and 166, respectively, of top valve body 102 by applying a solvent, such as cyclohexanone, to blood line connectors 164 and 166 and then sliding blood lines 206 and 208 over blood line connectors 164 and 166. Arterial and venous blood lines 212 and 214 can be connected to blood line connectors 136 and 138 of bottom valve body 104 using a similar technique. As an alternative to or in addition to applying a solvent to the blood line connectors, any of various other techniques can be used to secure the blood lines to the blood line connectors. For example, the blood lines can be thermally bonded and/or adhesively attached to the blood line connectors.

Blue bands 216 and 220 are secured to blood lines 208 and 214, respectively, and to blood line connectors 112 and 108, respectively. Red bands 218 and 222 are secured to blood lines 206 and 212, respectively, and to blood line connectors 110 and 106, respectively. The colored bands can be secured to the blood lines and the blood line connectors using any of various techniques. In some embodiments, the bands include a shoulder that has a diameter that is slightly greater than the outer diameter of its respective blood line connector and slightly less than the outer diameter of its respective blood line. In such embodiments, prior to securing the blood line to the blood line connector, the colored band can be slid over the blood line connector. The blood line can then be slid over the connector so that the colored band is compressed between the blood lien and the outer surface of the valve body. After the blood line is secured to the blood line connector, the colored band can be held in place between the blood line and the valve body.

When blue bands 216 and 220 are aligned with one another and red bands 218 and 222 are aligned with one another, as shown in FIG. 18, this indicates to the clinician that valve 100 is in the first position (e.g., the normal flow position). When blue band 216 is aligned with red band 222 and blue band 220 is aligned with red band 218, this indicates to the clinician that valve 100 is in the second position (e.g., the reversed flow position). If none of the bands are aligned with one another, this indicates to the clinician that valve 100 is in an intermediate position between the first and second positions.

While the bands have been described as being red and blue, any of various other colors can alternatively or additionally be used. Moreover, any of various other types of visual indicators can alternatively or additionally be displayed on the bands to help the clinician to identify the rotational position of valve 100. Examples of visual indicators include colors, letters, numbers, characters, patterns, etc.

When clear blood lines are used, the blood line connectors may themselves be colored. The coloring of the blood line connectors is generally visible through the clear tubes, providing a similar visual aid for determining the rotational position of valve 100. The blood line connectors can, for example, be colored using any of various coloring techniques, such as painting. Alternatively or additionally, the blood line connectors can be molded from one or more colored materials (e.g., colored plastics).

As described above, valve 100 also includes other types of alignment features. Top valve body 102 and bottom valve body 104 of valve 100, for example, include letters 141 and 189 and arrows 143 and 190. The letters and arrows, like the colored bands, can help the clinician to determine in what position valve 100 is disposed. For example, alignment of the letters and the arrows can indicate that valve 100 is in the first position (e.g., the standard flow position), and misalignment of the letters and arrows can indicate that valve 100 is in the second position or in an intermediate position between the first and second positions.

Figure 19A:
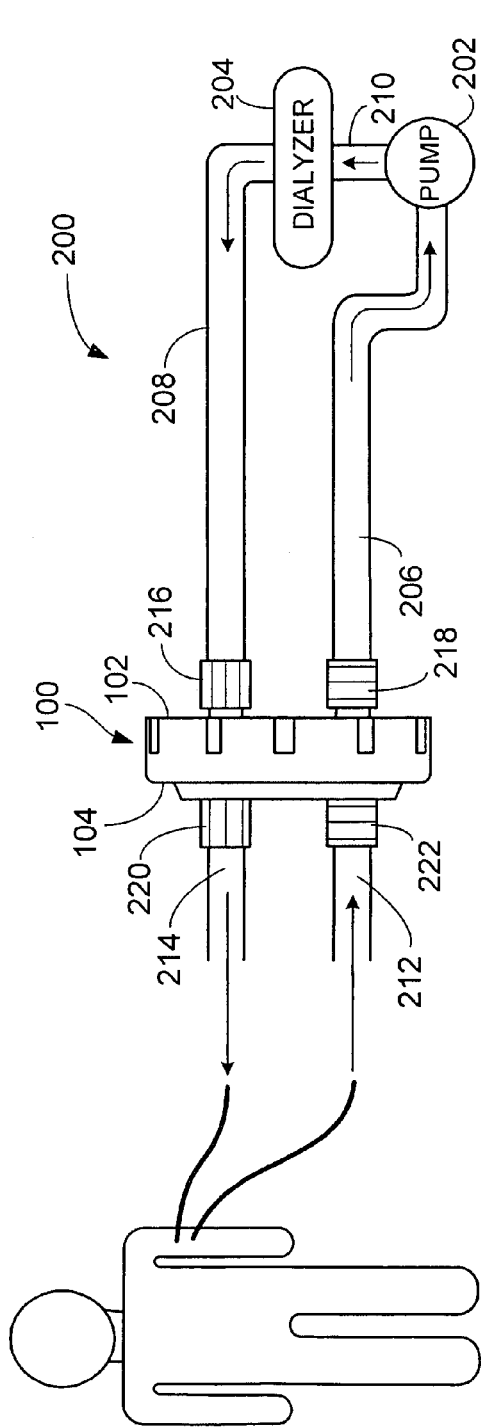
FIGS. 19A and 19B are similar schematic diagrams illustrating how the blood treatment system of FIG. 18 can be used to accomplish blood flow reversal in a hemodialysis patient, showing the valve of FIG. 1 in its normal and reversed orientation, respectively.
Figure 19B:
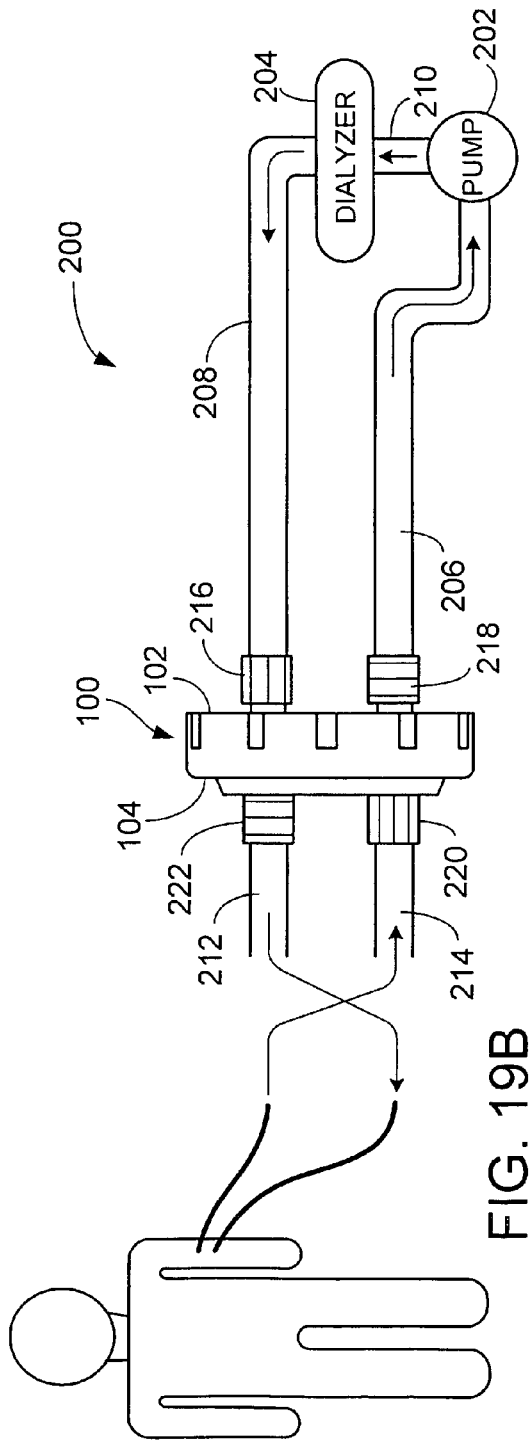

FIGS. 19A and 19B illustrate an exemplary method of using blood treatment system 200 to perform hemodialysis. Referring to FIG. 19A, arterial and venous blood lines 212 and 214 are connected to an artery and vein, respectively, of a subject. Any of various known methods can be used to connect arterial and venous blood lines 212 and 214 to the subject. For example, blood lines 212 and 214 can be fluidly connected to a fistula, graft or shunt implanted within a subject, which connects a vein of the subject to an artery of the subject. To begin treatment, valve 100 is configured in the first position, in which arterial blood line 212 is aligned with outlet blood line 206 and venous blood line 214 is aligned with inlet blood line 208. When in this position, as discussed above, blue bands 216 and 220 are aligned with one another and red bands 218 and 222 are aligned with one another to inform the clinician that valve 100 is in the first position. Pump 202 is then activated, causing blood to be drawn from the artery of the subject through arterial blood line 212 and outlet blood line 206 to pump 202. The blood is then forced through connection line 210 to blood treatment device 204, the blood is treated. After exiting blood treatment device 204, the blood continues through inlet blood line 208 and venous line 214 to the subject. The blood re-enters the vein of the subject via venous line 214. The blood is generally pumped through system 100 at a flow rate of approximately 300 ml/min. However, other flow rates are possible. Pump 202 can, for example, be configured to pump the blood at a rate of about 50 ml/min to about 600 ml/min.

As discussed above, it may be desirable at certain times during hemodialysis to reverse the flow of blood. Certain parameters can, for example, be measured in the standard flow and reversed flow configurations and compared to one another in order to determine the blood access flow rate. Examples of methods of determining blood access flow rates are described, for example, in U.S. Pat. Nos. 5,830,365 and 6,648,845, which are incorporated by reference herein.

In order to reverse the blood flow during the treatment, pump 202 is briefly stopped. The clinician then rotates top valve body 102 and bottom valve body 104 relative to one another until valve 100 reaches the reversed flow position (e.g., the second position) at which time an audible click and tactile feedback are produced along with visible confirmation from the aligned connectors. In the second position, blue band 216 is aligned with red band 222 and blue band 220 is aligned with red band 218, as shown in FIG. 19B. Thus, arterial blood line 212 is aligned with inlet blood line 208, and venous blood line 214 is aligned with outlet blood line 206. Pump 202 is then restarted, causing blood to be drawn from the vein of the subject and drawn through venous blood line 214 and outlet blood line 206 to pump 202. The blood is then passed through blood treatment device 204 to inlet blood line 208. The blood then passes through valve 100 to arterial blood line 221. The blood re-enters the artery of the subject via arterial blood line 212. During reversed flow, pump 202 pumps blood at a rate of about 300 ml/min. However, other flow rates are possible. Pump 202 can, for example, be configured to pump the blood at a rate of about 50 ml/min to about 600 ml/min during periods of reversed blood flow.

After the desired period of reversed blood flow is completed, pump 202 is again stopped and valve 100 is rotated back into the first position. Pump is then restarted, and the blood treatment is resumed.

Pump 202 can be any of various pumping devices capable of forcing blood through system 200. Examples of such pumping devices include peristaltic pumps, such as those available from Sarns, Inc. (Ann Arbor, Mich.).

Blood treatment device 204 can include any of various dialyzers. Examples of dialyzers include Fresenius Optiflux® series dialyzers.

Blood lines 206, 208, 210, 212, and 214 can be any of various types of blood lines. In some embodiments, the blood lines are formed of one or more compliant materials. Examples of materials from which the blood lines can be formed include polyvinylchloride (PVC), Di(2-ethylhexyl) phthalate (DEHP), polyolifins, etc.

While various embodiments have been described above, other embodiments are possible.

As an example, while the embodiments of valve 100 above describe projection 134 of top valve body 102 snapping into the detent formed between locking features 148 and stop 182 and between locking feature 150 and stop 184 to produce an audible click and tactile feedback, other techniques can alternatively or additionally be used to produce the audible click and/or tactile feedback. In some embodiments, for example, top valve body 102 can be equipped with a spring loaded ball and bottom valve body 104 can include a detent sized and shaped to receive the ball. In such embodiments, the rotational resistance provided can be a function of the size of the ball relative to the detent and the spring force applied to the ball by the spring.

As another example, while in the embodiments described above valve 100 was configured to be fixed in two positions (the first and second positions), valve 100 can alternatively be configured to be fixed in three or more positions. For example, two additional circumferentially spaced locking features can be located between locking features 148 and 150 so that valve 100 can be fixed in a third position that is intermediate to the first and second positions. Valve 100 can be arranged such that the ports of top valve body 102 are not aligned with the ports of bottom valve body 104 when valve is in the third position. Consequently, the flow of blood through valve 100 can be substantially prevented in the third position.

As an additional example, while each of top valve body 102 and bottom valve body 104 has been described as including two fluid passages or ports, top valve body 102 and bottom valve body 104 can include three or more ports. The ports can, for example, be circumferentially spaced by equal distances and positioned equidistant from the center such that any of the various ports can be aligned with one another by rotating top valve body 102 and bottom valve body 104.

As a further example, while embodiments of top valve body 102 have been described in which projection 134 extends from the inner surface of top valve body 102, projection 134 can alternatively or additionally be positioned at other locations within top valve body 102. For example, projection 134 can extend from side wall 128 of top valve body 102. Moreover, while the embodiments described above relate to top valve body 102, which includes projection 134, and bottom valve body 104, which includes stops 182 and 184 and locking features 148 and 150, top valve body 102 can alternatively or additionally include a stop and locking features, and bottom valve body 104 can alternatively or additionally include a resilient projection configured to be seated between the locking features and stops.

As another example, while gasket 114 has been described as being secured to bottom valve body 104 using protruding features that mate with recessed features of bottom valve body 104, other techniques can be used. Examples of other securing techniques include thermal bonding, adhesive bonding, and mechanical fasteners.

As an additional example, while gasket 114 has been described as being secured to bottom valve body 104, gasket can alternatively be secured to top valve body 102.

As a further example, while valve 100 has been described as including gasket 114 between top valve body 102 and bottom valve body 104, in other embodiments, valve 100 need not include a gasket. In such embodiments, top valve body 102 and bottom valve body 104 can be configured and designed to mate with one another to form a substantially fluid tight seal.

As another example, while the embodiments above describe top valve body 102 as including center pin 122, which fits into cylindrical passage 162 of bottom valve body 104 to secure top valve body 102 and bottom valve body 104 to one another, other techniques can alternatively or additionally be used to secure top valve body 102 and bottom valve body 104 together. In certain embodiments, for example, top valve body 102 and bottom valve body 104 are snap fitted together only from their outer circumferences using retaining members 135. In some embodiments, other types of securing devices or mechanisms can be used. For example, other types of mechanical fasteners can be used to secure the top valve body and bottom valve body together.

As a further example, while embodiments of valve 100 have been described in which valve 100 is configured to produce an audible click and tactile feedback when rotated into the first and second positions, and in which valve 100 further includes alignment features to help the clinician identify the position in which valve 100 is disposed, other configurations are possible. Valve 100 can, for example, include only one or two of the above-noted features.

As an additional example, while resilient fingers 126 of center pin 122 have been described as deflecting inward as center pin 122 is inserted through central aperture 162, the surfaces of bottom valve body 104 that form aperture 162 can alternatively or additionally be configured to deflect outward in response to center pin 122 being inserted through aperture 162.

As a further example, while fingers 126 of center pin 122 have been described as being resilient, in certain embodiments fingers 126 are relatively rigid. In such embodiments, fingers 126 can outwardly deflect the surfaces of bottom valve body 104 that define aperture 162 as center pin 122 is inserted through aperture 162. Alternatively or additionally, fingers 126 can core through a portion of the surface of bottom valve body 104 that forms aperture 162 as center pin 122 is inserted through aperture 162. Ridged portions of fingers 126 can, for example, both stretch and core the surfaces defining aperture 162 of bottom valve body 104 as top valve body 102 and bottom valve body 104 are pressed together. The coring that takes place generally causes about 0.25 millimeter or less of material to be removed from portions of bottom valve body 104 that define aperture 162. The removed material is pushed toward the outer surface of bottom valve body 104 as the ridged portions of center pin 122 are forced through aperture 162. The removed material creates circumferentially spaced apart lands around aperture 126. After the ridged portions of fingers 126 have cleared aperture 126, aperture 126 closes back toward its original dimensions. Consequently, shoulder regions of fingers 126 sit atop the lands to prevent top valve body 102 and bottom valve body 104 from being separated from one another. Top valve body 102 can also be rotated such that the shoulder regions of fingers 126 are rotated along and rest on shelf portions of bottom valve body 104 that have not experienced coring. Thus, top valve body 102 and bottom valve body 104 can be prevented from becoming separated from one another along their entire range of rotation relative to one another.

As another example, while valve 100 has been described as a component for a hemodialysis systems, valve 100 can alternatively or additionally be used with other types of blood treatment systems where flow reversal is desired. Examples of other types of blood treatment systems include plasmapheresis, autotransfusion devices, and hemoabsorptive devices.

Other embodiments are in the claims.

What is claimed is:

1. A blood flow reversal valve for extracorporeal blood lines, the blood flow reversal valve comprising:

a first valve portion defining first and second ports extending therethrough;

a second valve portion defining first and second ports extending therethrough, the valve portions being rotatably secured to one another, the valve portions being configured to be rotated into a first position in which the first ports are aligned with one another and the second ports are aligned with one another; and a disk-shaped gasket disposed between the first and second valve portions, the disk-shaped gasket being substantially rotationally fixed relative to one of the first and second valve portions such that the first and second ports of the one of the first and second valve portions are maintained in alignment with first and second ports defined by the disk-shaped gasket when the first and second valve portions are rotated relative to one another, wherein the second valve portion comprises a detent mechanism comprising two raised members that are circumferentially spaced from one another, and the first valve portion comprises a projection adapted to fit securely between the raised members when the valve portions are in the first position, wherein an inner surface of one of the first and second valve portions defines first and second annular channels, and the disk-shaped gasket comprises first and second annular raised features extending from a surface of the gasket, the first and second annular raised features arranged concentrically with respect to one another with the first annular raised feature extending along a perimeter region of the disk-shaped gasket and the second annular raised feature extending from a central region of the disk-shaped gasket, the first annular raised feature configured to extend into the first annular channel, and the second annular raised feature configured to extend into the second annular channel, wherein one of the first and second valve portions comprises multiple resilient retaining members that extend inwardly from and are circumferentially spaced around a side wall of the one of the first and second valve portions, the multiple resilient members being configured to cooperate with a surface of the other of the first and second valve portions to secure the first and second valve portions to one another and to provide a first compressive force to the perimeter of the disk-shaped gasket, and one of the first and second valve portions comprises a center pin extending along a rotational axis of the one of the first and second valve portions, the center pin being configured to cooperate with a surface of the other of the first and second valve portions to rotatably secure the first and second valve portions to one another and to provide a second compressive force to the central region of the disk-shaped gasket.

2. The blood flow reversal valve of claim 1, wherein one of the raised members is a stop configured to prevent the first and second valve portions from being rotated relative to one another beyond a predetermined position.

3. The blood flow reversal valve of claim 1, wherein the raised members extend from a side surface of the second valve portion.

4. The blood flow reversal valve of claim 3, wherein the projection extends from an inner surface of the first valve portion.

5. The blood flow reversal valve of claim 1, wherein the projection is configured to snap into engagement with the detent mechanism when the first and second valve portions are rotated into the first position.

6. The blood flow reversal valve of claim 5, wherein the snapping of the projection into engagement with the detent mechanism produces an audible click.

7. The blood flow reversal valve of claim 1, wherein the valve portions are constructed to provide tactile feedback to a clinician when the clinician manually rotates the valve portions into the first position.

8. The blood flow reversal valve of claim 1, wherein the valve portions are constructed to be substantially rotationally fixed relative to one another in the first position.

9. The blood flow reversal valve of claim 1, wherein the first and second valve portions are further configured to be rotated into a second position in which the first port of the first valve portion is aligned with the second port of the second valve portion and the second port of the first valve portion is aligned with the first port of the second valve portion.

10. The blood flow reversal valve of claim 9, wherein the second valve portion comprises first and second detent mechanisms that are circumferentially spaced from one another by approximately 180 degrees.

11. The blood flow reversal valve of claim 10, wherein the projection is configured to engage the first detent mechanism when the valve portions are in the first position and the projection is configured to engage the second detent mechanism when the valve portions are in the second position.

12. The blood flow reversal valve of claim 9, wherein the valve portions are constructed to be substantially rotationally fixed relative to one another in the first and second positions.

13. The blood flow reversal valve of claim 1, wherein the first and second valve portions are substantially disk-shaped, and coaxially rotatably connected to each other.

14. The blood flow reversal valve of claim 1, wherein the first and second valve portions are rotatable to a third position in which none of the ports of the first and second valve portions are aligned with one another such that blood is substantially prevented from passing from the first valve portion to the second valve portion when the first and second valve portions are in the third position.

15. The blood flow reversal valve of claim 1, wherein each of the valve portions comprises an alignment feature, the alignment features being arranged to align with one another when the valve portions are in the first position.

16. The blood flow reversal valve of claim 15, wherein the first and second valve portions further comprise blood line connectors configured to fluidly connect blood lines to the first and second valve portions, the alignment features being disposed on the blood line connectors.

17. The blood flow reversal valve of claim 16, wherein the alignment features comprise bands adapted to be secured to the blood line connectors.

18. The blood flow reversal valve of claim 1, wherein the projection is configured to slide over one of the raised members when the first and second valve portions are rotated into the first position.

19. The blood flow reversal valve of claim 18, wherein the projection is configured to deflect when the projection is slid over the one of the raised members.

20. The blood flow reversal valve of claim 18, wherein the projection and the one of the raised members are configured to increase rotational resistance of the first valve portion relative to the second valve portion when the projection is slid over the one of the raised members.

21. The blood flow reversal valve of claim 1, wherein the center pin comprises multiple, circumferentially spaced resilient fingers.

22. The blood flow reversal valve of claim 1, wherein the disk- shaped gasket is substantially rotationally fixed relative to the one of the first and second valve portions and the first annular channel is defined by the inner surface of the other of the first and second valve portions.

23. The blood flow reversal valve of claim 1, wherein the disk-shaped gasket is at least partially disposed within a recessed region defined by the one of the first and second valve portions, the recessed region being arranged to substantially prevent the disk- shaped gasket from rotating relative to the one of the first and second valve portions.

24. The blood flow reversal valve of claim 1, wherein the disk-shaped gasket covers substantially an entire inner surface of the one of the first and second valve portions.

25. The blood flow reversal valve of claim 1, wherein first and second annular rims extend from an inner surface of one of the first and second valve portions, the first and second annular rims surrounding the first and second ports, respectively, of the one of the first and second valve portions, the first and second annular rims being arranged to cooperate with the disk-shaped gasket to form a fluid-tight seal.

26. A blood flow reversal valve for extracorporeal blood lines, the blood flow reversal valve comprising:
   a first valve portion defining first and second ports extending therethrough; and
   a second valve portion defining first and second ports extending therethrough, the first and second valve portions being rotatable relative to one another between a first engaged position and a second engaged position, the first and second valve portions being substantially rotationally fixed relative to one another when the first and second valve portions are in the first and second engaged positions; and
   a disk-shaped gasket disposed between the first and second valve portions, the disk-shaped gasket being substantially rotationally fixed relative to one of the first and second valve portions such that first and second ports of the one of the first and second valve portions are maintained in alignment with first and second ports defined by the disk-shaped gasket when the first and second valve portions are rotated relative to one another,
   wherein an inner surface of one of the first and second valve portions defines first and second annular channels, and the disk-shaped gasket comprises first and second annular raised features extending from a surface the gasket, the first and second annular raised features arranged concentrically with respect to one another with the first annular raised feature extending along a perimeter of the disk-shaped gasket and the second annular raised feature extending from a central region of the disk-shaped gasket, the first annular raised feature configured to extend into the first annular channel, and the second annular raised feature configured to extend into the second annular channel,
   wherein one of the first and second valve portions comprises multiple resilient retaining members that extend inwardly from and are circumferentially spaced around a side wall of the one of the first and second valve portions, the multiple resilient members being configured to cooperate with a surface of the other of the first and second valve portions to secure the first and second valve portions to one another and to provide a first compressive force to the perimeter of the disk-shaped gasket, and one of the first and second valve portions comprises a center pin extending along a rotational axis of the one of the first and second valve portions, the center pin being configured to cooperate with a surface of the other of the first and second valve portions to rotatably secure the first and second valve portions to one another and to provide a second compressive force to the central region of the disk-shaped gasket, wherein each of the first and second valve portions comprises at least one alignment feature, the alignment features being arranged to align with one another when the valve portions are in one of the engaged positions.

27. The blood flow reversal valve of claim 26, wherein the alignment features comprise visual indicators.

28. The blood flow reversal valve of claim 26, wherein each of the valve portions comprises first and second alignment features, the first alignment features being dissimilar to the second alignment features.

29. The blood flow reversal valve of claim 28, wherein the first alignment features are aligned with one another in the first engaged position.

30. The blood flow reversal valve of claim 29, wherein the first alignment feature of the first valve portion is aligned with the second alignment feature of the second valve portion when the valve portions are in the second engaged position.

31. The blood flow reversal valve of claim 26, wherein the first and second valve portions comprise blood line connectors extending from outer surfaces of the valve portions, and the alignment features comprise visual indicators disposed on the blood line connectors.

32. The blood flow reversal valve of claim 31, wherein the alignment features comprise colored bands.

33. The blood flow reversal valve of claim 26, wherein the second valve portion comprises at least two detent mechanisms, each detent mechanism comprising two raised members, the projection being configured fit securely between the raised members of the first and second detent mechanisms when the valve portions are in the first and second engaged positions, respectively, to substantially rotationally fix the first valve portion relative to the second valve portion.

34. The blood flow reversal valve of claim 33, wherein the projection and detent mechanisms are configured so that, when the first and second valve portions are in the first or second engaged position, the first valve portion is prevented from rotating relative to the second portion until a predetermined rotational force is applied to one of the first and second valve portions relative to the other of the first and second valve portions.

35. The blood flow reversal valve of claim 26, wherein the center pin comprises multiple, circumferentially spaced resilient fingers.

36. The blood flow reversal valve of claim 26, wherein the disk-shaped gasket is substantially rotationally fixed relative to the one of the first and second valve portions and the first annular channel is defined by the inner surface of the other of the first and second valve portions defines.

37. The blood flow reversal valve of claim 26, wherein the disk-shaped gasket is at least partially disposed within a recessed region defined by the one of the first and second valve portions, the recessed region being arranged to substantially prevent the disk-shaped gasket from rotating relative to the one of the first and second valve portions.

38. The blood flow reversal valve of claim 26, wherein the disk-shaped gasket covers substantially an entire inner surface of the one of the first and second valve portions.

39. The blood flow reversal valve of claim 26, wherein first and second annular rims extend from an inner surface of one of the first and second valve portions, the first and second annular rims surrounding the first and second ports, respectively, of the one of the first and second valve portions, the first and second annular rims being arranged to cooperate with the disk-shaped gasket to form a fluid-tight seal.

* * * * *